(12) United States Patent
Basta et al.

(10) Patent No.: US 12,708,463 B2
(45) Date of Patent: Aug. 18, 2026

(54) HUMERAL CLAMPS FOR NAVIGATED SHOULDER ARTHROPLASTY

(71) Applicant: Orthosoft ULC, Montreal (CA)

(72) Inventors: Ian Basta, Montreal (CA); Alexis Balli, Montreal (CA); Jeremie Menard, Montreal (CA); Karine Dupuis, Montreal (CA); Yann Zimmermann, Montreal (CA); Aiden Reich, Montreal (CA); Ajith Airody, L'Île-Bizard (CA); Bruno Chabot, Montreal (CA); VanGiau Luu, St-Leonard (CA); Trong-Tin Nguyen, Laval (CA); Louis-Philippe Amiot, Montreal (CA); Maxime Besson, Montreal (CA)

(73) Assignee: Orthosoft ULC, Montreal (CA)

( * ) Notice: Subject to any disclaimer, the term of this patent is extended or adjusted under 35 U.S.C. 154(b) by 914 days.

(21) Appl. No.: 17/949,864

(22) Filed: Sep. 21, 2022

(65) Prior Publication Data

US 2023/0094132 A1 Mar. 30, 2023

Related U.S. Application Data

(60) Provisional application No. 63/291,833, filed on Dec. 20, 2021, provisional application No. 63/248,869, filed on Sep. 27, 2021.

(51) Int. Cl.

| | |
|---|---|
| ***A61B 34/30*** | (2016.01) |
| ***A61B 90/00*** | (2016.01) |
| *A61B 34/20* | (2016.01) |

(52) U.S. Cl.

CPC .............. *A61B 34/30* (2016.02); *A61B 90/39* (2016.02); *A61B 2034/2055* (2016.02); *A61B 2090/3983* (2016.02)

(58) Field of Classification Search

CPC ........................................................ A61B 17/82

See application file for complete search history.

(56) References Cited

U.S. PATENT DOCUMENTS

| | | | |
|---|---|---|---|
| 8,386,022 | B2 | 2/2013 | Jutras et al. |
| 10,932,837 | B2 | 3/2021 | Moctezuma De la Barrera et al. |

(Continued)

FOREIGN PATENT DOCUMENTS

| | | |
|---|---|---|
| WO | WO-2016044934 A1 | 3/2016 |

OTHER PUBLICATIONS

"European Application Serial No. 22197229.2, Extended European Search Report mailed Feb. 7, 2023", 7 pgs.

(Continued)

*Primary Examiner* — Andrew Yang
(74) *Attorney, Agent, or Firm* — SCHWEGMAN LUNDBERG & WOESSNER, P.A.

(57) ABSTRACT

A device for registering a bone for a robotic shoulder arthroplasty with a surgical robot. The device can include a first portion engageable with a first portion of a bone and can include a second portion engageable with a second portion of the bone, the second portion connected to the first portion and rotatable with respect to the first portion. The device can include a registration device connectable to the first portion and configured to interface with the surgical robot for registration of the device and the bone. The device can include an actuator engageable with the first portion and the second portion to move the second portion toward a closed position away from an open position.

17 Claims, 34 Drawing Sheets

(56) References Cited

U.S. PATENT DOCUMENTS

| | | | | |
|---|---|---|---|---|
| 10,959,857 | B2 | 3/2021 | Wu et al. | |
| 2009/0024127 | A1 * | 1/2009 | Lechner ................. | A61B 90/39<br>606/53 |
| 2009/0270928 | A1 | 10/2009 | Stone et al. | |
| 2010/0210939 | A1 | 8/2010 | Hartmann et al. | |
| 2018/0092667 | A1 | 4/2018 | Heigl et al. | |

OTHER PUBLICATIONS

"European Application Serial No. 22197229.2, Response filed Sep. 21, 2023 to Extended European Search Report mailed Feb. 7, 2023", 92 pgs.

Giordano, Md, Gerard, et al., "ExactechGPS RTKA Operative Technique", Exactech, Inc. 712-32-30 Rev. B 0621, (2021), 50 pgs.

"European Application Serial No. 22197229.2, Communication Pursuant to Article 94(3) EPC mailed Sep. 29, 2025", 4 pgs.

* cited by examiner 202
200
50

50
202

202
240
200
50

50
202
200

204
202
200
50

204
202
200
50

HUMERAL CLAMPS FOR NAVIGATED SHOULDER ARTHROPLASTY

CLAIM OF PRIORITY

This application claims the benefit of U.S. Provisional Patent Application Ser. No. 63/248,869, filed on Sep. 27, 2021, and also claims the benefit of U.S. Provisional Patent Application Ser. No. 63/291,833, filed on Dec. 20, 2021, the benefit of priority of each of which is claimed hereby, and each of which is incorporated by reference herein in its entirety.

BACKGROUND

Implants are commonly used to replace various components of a human body, such as bones, bone joints, or tissues. Joint replacement procedures include shoulder replacement procedures (or shoulder arthroplasties), hip replacement procedures (or hip arthroplasties), or knee replacement procedures (knee arthroplasty). In robotic joint replacement procedures, navigational systems are used to help guide a surgeon or to perform operations. During a shoulder arthroplasty, for example, a registration marker can be secured to a humerus.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Computer-assisted surgery has been developed to help surgeons alter bones, and to position or orient implants to a desired location. Computer-assisted surgery may encompass a wide range of devices, including surgical navigation, pre-operative planning, and various robotic devices. Many conventional techniques of joint arthroplasties do not use a robot, which can result in errors or can lack precision. Robotic-assisted surgical systems can help to reduce errors and increase precision. In a robotic-assisted surgery, tracking or navigation devices can be used to help improve determination of a location of bones and instruments by the robotic surgical systems to help improve accuracy of positioning or cutting operations performed, in part or in whole, by the robotic surgical system. However, the tracking devices must be able to accommodate bones of various sizes to ensure proper fixation to the bone. Further, placement of standard pins can interfere with operations performed during a procedure, such as reaming of a tibia of femur. Also, many or most current clamp systems are based on the needs of knee arthroplasty and are affixed medially and laterally to the bone.

This disclosure can help to address these issues by including specialized instruments that allow for standard reference arrays to be secured to bones during a robotic surgical procedure. For example, a bone plate can be securable to a humerus using bone spikes and a surgical cable to help limit penetration depth and to help avoid interference with reaming and implantation operations. The plate can include a registration marker connected thereto so that the optical navigation tracking system can identify and locate the plate to locate the bone within space, allowing the robotic surgical system to accurately track the location of the bones during a robotic-assisted surgical procedure. The plate can also help to address a need of shoulder arthroplasty by being used for anterior, posterior, or lateral fixation.

The above discussion is intended to provide an overview of subject matter of the present patent application. It is not intended to provide an exclusive or exhaustive explanation of the invention. The description below is included to provide further information about the present patent application.

Figure 1A:
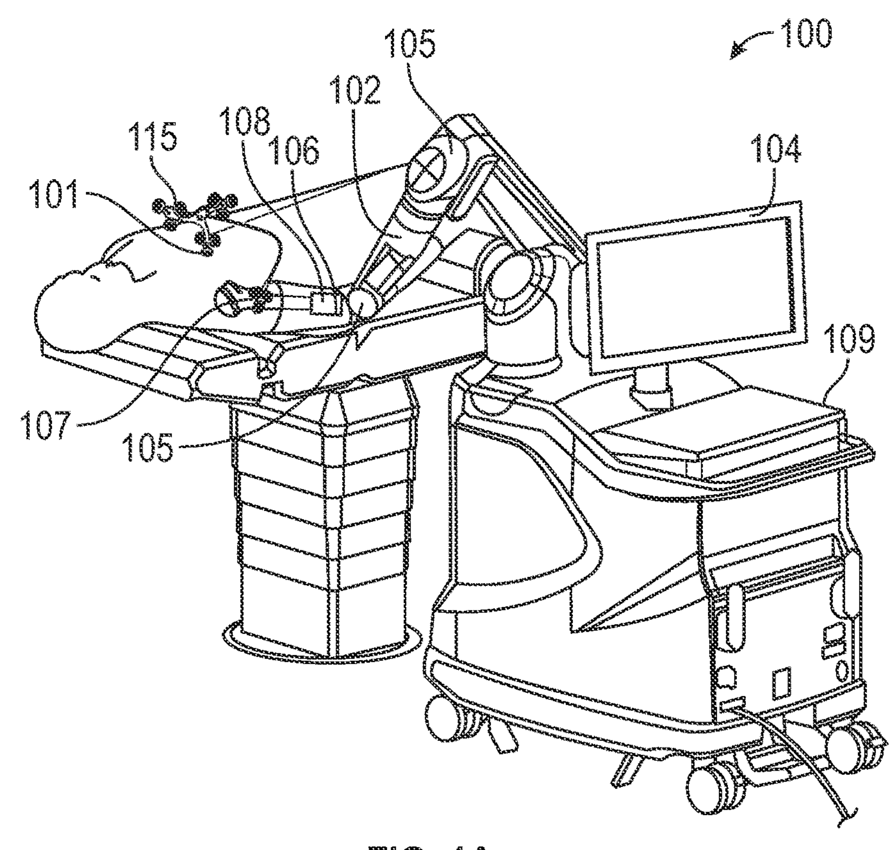
FIG. 1A illustrates a perspective view of a robotic surgical system.
Figure 1B:
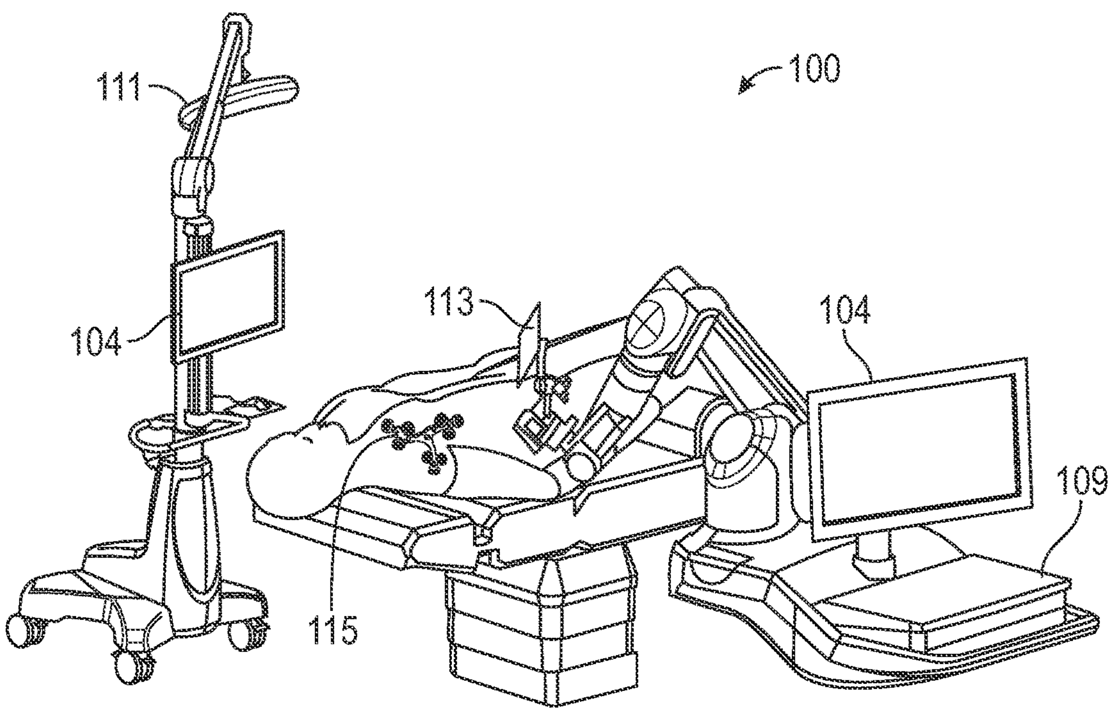
FIG. 1B illustrates a perspective view of a robotic surgical system.

FIG. 1A illustrates a perspective view of a robotic surgical system 100 including a coupler system 101 coupled to a robotic arm 102. FIG. 1B illustrates an isometric view of the robotic surgical system 100. FIGS. 1A and 1B are discussed together below.

The robotic arm 102 can be a 6 degree-of-freedom (DOF) robot arm, such as the ROSA® robot from Medtech, a Zimmer Biomet Holdings, Inc. company. The robotic arm 102 can be controlled by a surgeon with various control devices or systems. For example, a surgeon can use a control system (e.g., a controller that is processor-implemented based on machine-readable instructions, which when implemented cause the robotic arm to move automatically or to provide force assistance to surgeon-guided movement) to guide the robotic arm 102. The robotic arm 102 can include two or more articulating joints 105 capable of pivoting, rotating, or both, to provide a surgeon with wide range of adjustment options. A surgeon can also use anatomical imaging, such as displayed on a display screen 104, to guide and position the robotic arm 102. Anatomical imaging can be provided to the display screen 104 with various imaging sources, such as one or more cameras positioned on the coupler system 101, or intraoperative fluoroscopy, such as a C-arm.

The robotic arm 102 can be controlled by a surgeon with various control devices or systems. For example, a surgeon can use a control system (e.g., a controller that is processor-implemented based on machine-readable instructions, which when implemented cause the robotic arm to move automatically or to provide force assistance to surgeon-guided movement) to guide the robotic arm 102. The robotic arm 102 can include two or more articulating joints 105 capable of pivoting, rotating, or both, to provide a surgeon with wide range of adjustment options. A surgeon can also use anatomical imaging, such as displayed on a display screen 104, to guide and position the robotic arm 102. Anatomical imaging can be provided to the display screen 104 with various imaging sources, such as one or more cameras, or intraoperative fluoroscopy, such as a C-arm.

The anatomical imaging, for example, can be imaging of internal patient anatomy within an incision 107. The incision 107 can be made in a variety of positions on a patient. For example, in a shoulder arthroplasty procedure, the incision 107 can be made in a shoulder region of a patient. The incision 107 can be configured to allow one or more tools coupled to the robotic arm 102 to access a bone surface, or other anatomy of the patient. The robotic arm 102 can include an end effector 106. The end effector 106 can include an instrument 108 (such as a reamer, impactor, placement tool, guide, or the like), which can be coupled to the robotic arm 102.

The robotic system 100 can include a computing system 109, which can also communicate with display screens 104 and a tracking system 111 (shown in FIG. 1B). The tracking system 111 can be operated by the computing system 109 as a stand-alone unit. The computing system 109 can optionally utilize the Polaris optical tracking system from Northern Digital, Inc. of Waterloo, Ontario, Canada. The tracking system 111 can monitor a plurality of tracking elements, such as tracking elements 113 (shown in FIG. 1B). The tracking elements 113 can be affixed to objects of interest, to track locations of multiple objects within a surgical field.

The tracking system 111 can function to create a virtual three-dimensional coordinate system within the surgical field for tracking patient anatomy, surgical instruments, or portions of the end effector 106 or robotic arm 102. The registration devices 115 can optionally be connected to bones or instruments. Optionally, as discussed in further detail below, the registration devices 115 can be removably connectable (such as non-permanently connected) to bones of the patient. The registration devices 115 can be tracking devices that can include multiple IR, reflective tracking spheres, or similar optically tracked marker devices, such as the NavitrackER® Reference Marker by Zimmer Biomet, or such as those described and discussed in U.S. Pat. No. 8,386,022, which is incorporated herein by reference in its entirety.

In one example, the registration devices 115 can be placed on or adjacent one or more bones of patient. In other examples, the registration devices 115 can be placed on the end effector 106 and/or an implant to accurately track positions within the virtual coordinate system. In each instance the registration devices 115 can provide position data, such as a patient position, a bone position, a joint position, an implant position, a position of the robotic arm 102, or the like.

Figure 2:
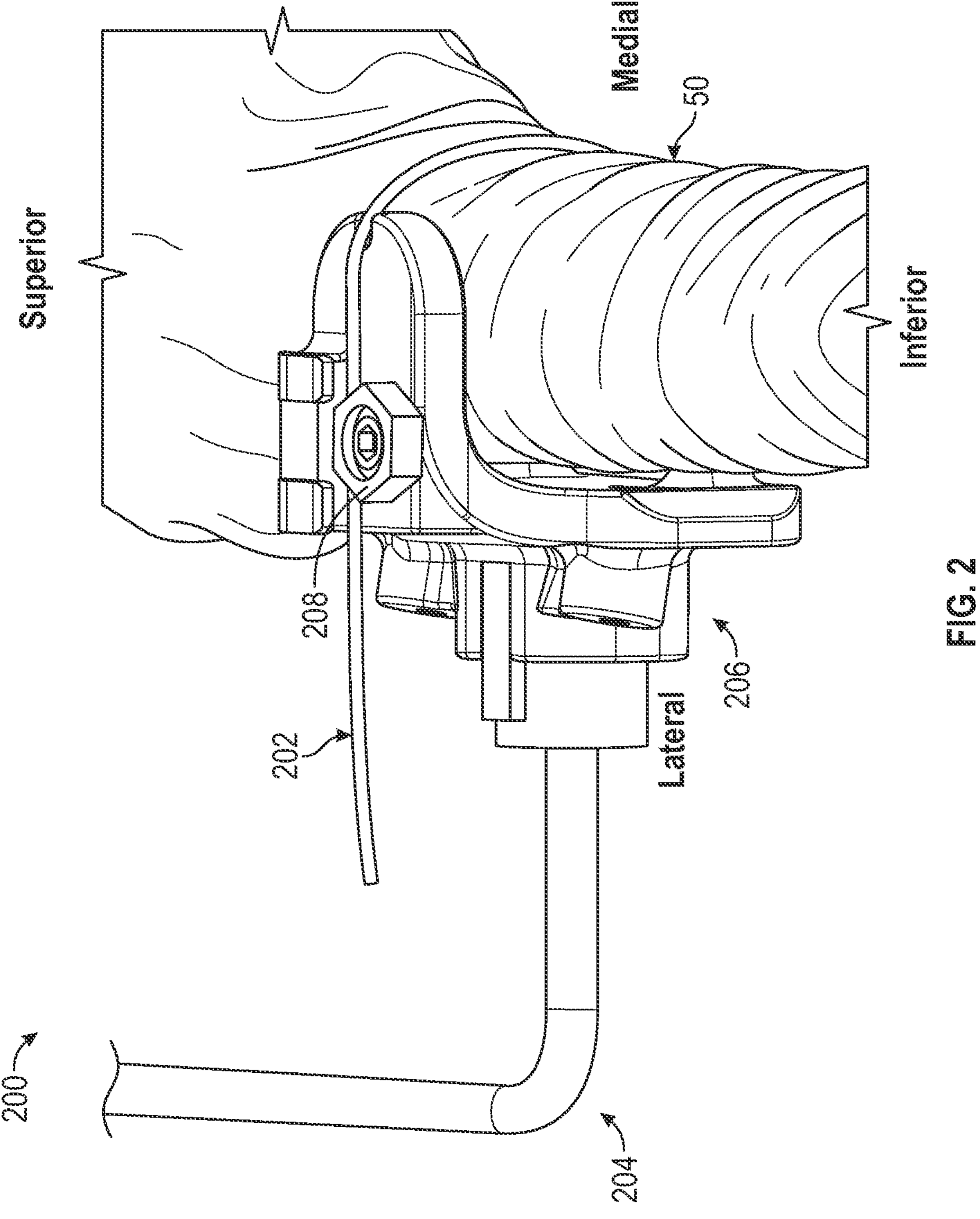
FIG. 2 illustrates an isometric view of a portion of a registration device for a robotic surgical system.

FIG. 2 illustrates an isometric view of a portion of a registration assembly 200 for a robotic surgical system, such as the system 100. The registration assembly 200 can include a surgical cable 202, a registration device 204, and a plate 206. FIG. 2 also shows a humerus 50 and orientation indicators Superior, Inferior, Medial, and Lateral.

The surgical cable 202 can be a surgical cable, tie, or the like configured to secure at least a portion of a bone or other element. The surgical cable 202 can be made of one or more of metals, polymers, or the like, and can be optionally made of biocompatible materials (e.g., titanium or cobalt chromium). At least a portion of the surgical cable 202 can be connected to the plate 206.

The registration device 204 can be a component of an optical tracking system such as the tracking system 111, and can function to create a virtual three-dimensional coordinate system within the surgical field for tracking patient anatomy, surgical instruments. The registration device 204 can include multiple IR reflective tracking spheres, or similar optically tracked marker devices. The registration device 204 can be connected to the plate 206 and can be optionally removably connectable to the plate 206. In operation, the registration device 204 can be configured to interface with the robotic system 100 for registration of the plate 206 and the bone 50.

The plate 206 can be engageable with an outer surface of the humerus 50, but can be configured to be engaged with or secured to other bones such as femurs, tibias, or the like. The plate 206 can be made of one or more of metals, polymers, or the like, and can be optionally made of biocompatible materials (e.g., titanium or cobalt chromium). The registration assembly 200 can also include a locking device 208 connected to the plate 206 and engageable with the surgical cable 202 to secure at least a portion of the surgical cable 202 to the plate 206.

In operation, the registration assembly 200 can be secured to the humerus 50 using the surgical cable 202. Additionally, the plate 206 can include one or more traction features (e.g., bone spikes) engageable with the humerus 50 to help limit movement of the plate 206 with respect to the humerus 50. Once the surgical cable 202 is positioned as desired, a free end of the surgical cable 202 can be engaged with the locking device 208. The locking device 208 can then be operated to tension or lock the surgical cable 202 to the plate 206 to help limit movement of the registration assembly 200 with respect to the humerus 50. Also, as shown in FIG. 2, the registration assembly 200 can be secured to a lateral portion of the humerus 50 close to the resection line, which can help to limit additional incisions and can help to increase accuracy as the registration device 204 is located relatively close to the humeral head.

Figure 3A:
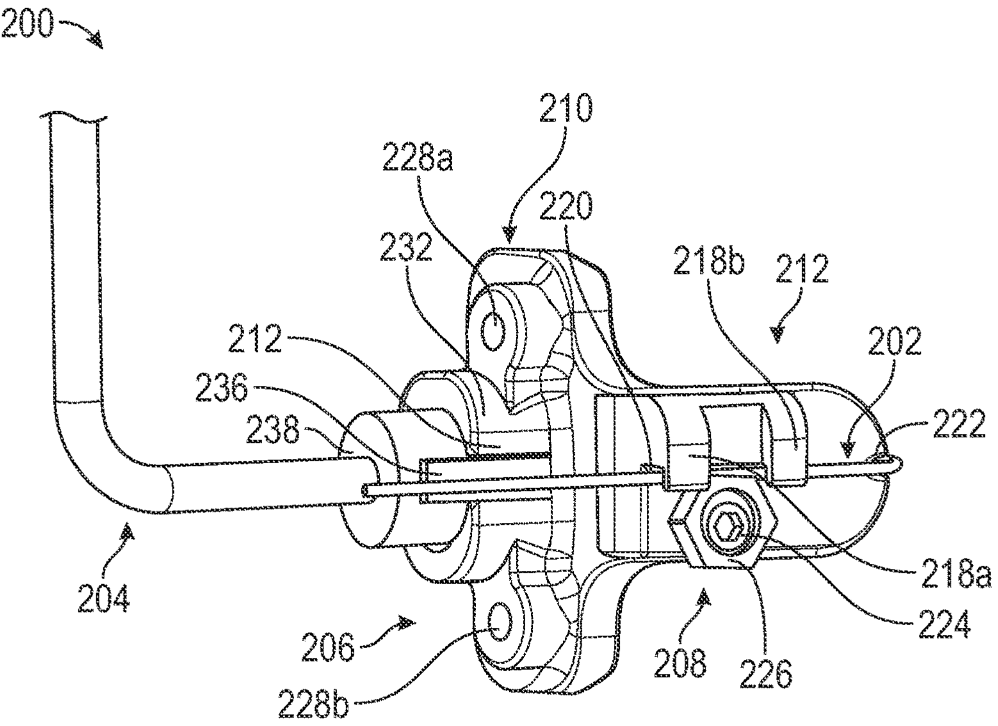
FIG. 3A illustrates an isometric view of a portion of a registration assembly for a robotic surgical system.

FIGS. 3A-3D illustrate isometric views of a portion of the registration assembly 200 for a robotic surgical system. FIGS. 3A-3D are discussed together below. The registration assembly 200 of FIGS. 3A-3D can be similar to the registration assembly 200 discussed above with respect to FIG. 2; FIGS. 3A-3D can show additional details of the registration assembly 200. For example, FIG. 3A shows that the plate 206 can include a first portion 210 and a second portion 212 where the first portion 210 and the second portion 212 can be connected to each other at an angle, such as at 60 degrees. 70 degrees, 80 degrees, 90 degrees, 100 degrees, 110 degrees, 120 degrees, or the like. Optionally, the first portion 210 or the second portion 212 can be curved. The first portion 210 and the second portion 212 can be together configured to engage adjacent portions of a bone, such as a lateral portion and an anterior portion of a humerus, as shown in FIG. 2. Optionally, the first portion 210 and the second portion 212 can engage other portions of other bones.

Figure 3B:
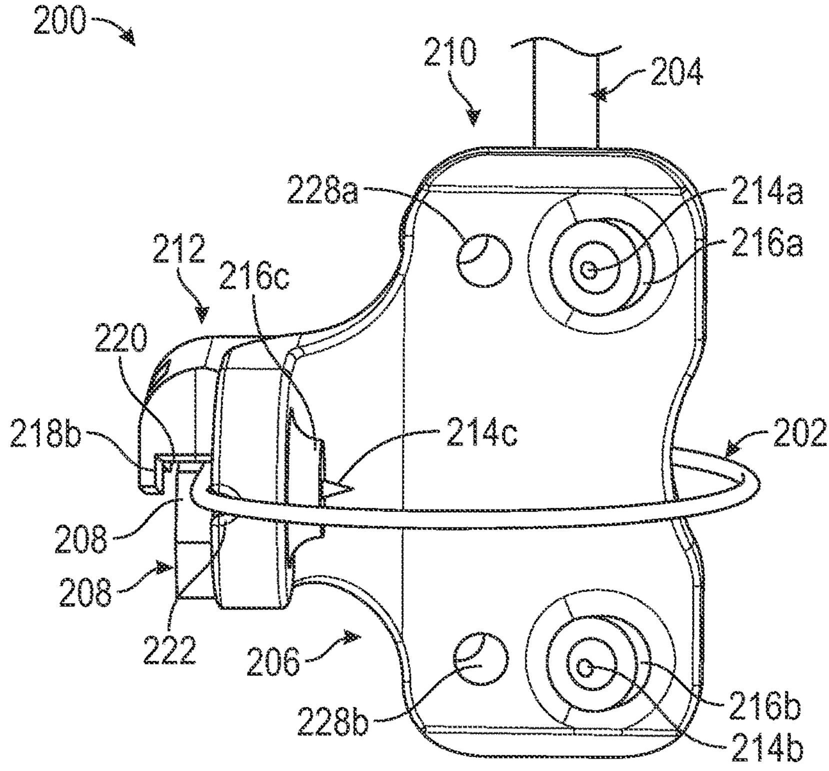
FIG. 3B illustrates an isometric view of a portion of a registration assembly for a robotic surgical system.
Figure 3C:
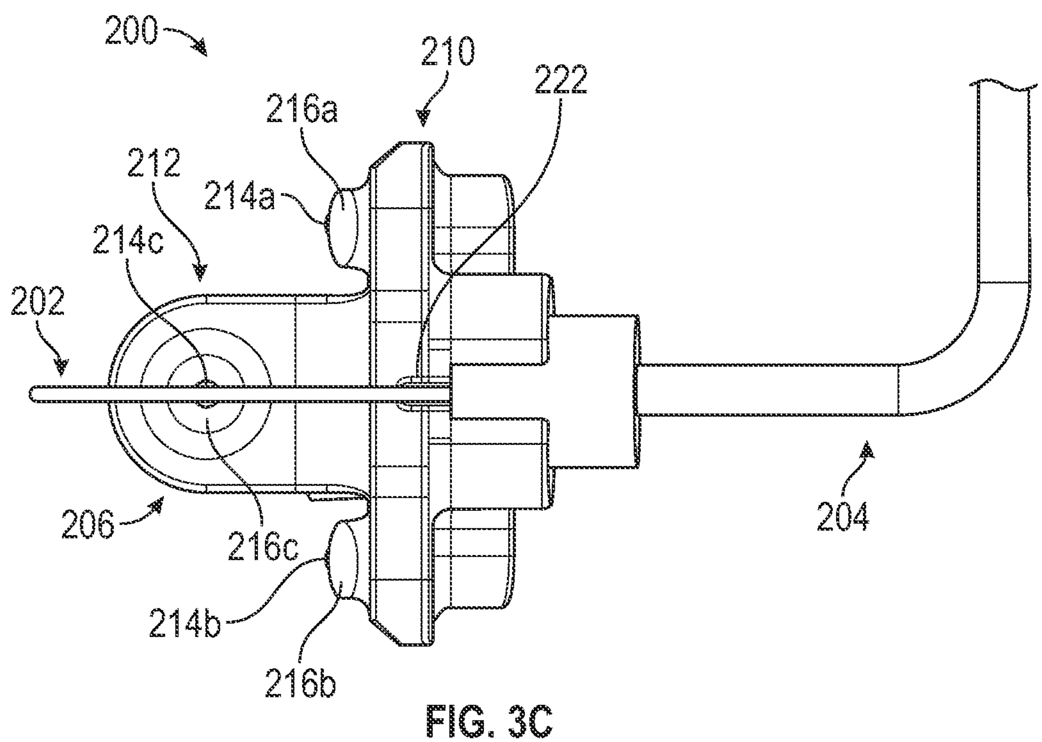
FIG. 3C illustrates an isometric view of a portion of a registration assembly for a robotic surgical system.

The first portion 210 can include a bone spike 214*a* and a bone spike 214*b*, and the second portion 212 can include a bone spike 214*c* (collectively referred to as bone spikes 214), as shown in FIG. 3B. The bone spikes 214 can each be configured to engage and partially penetrate a bone, such as the humerus 50, such as to help maintain a position and orientation of the registration assembly 200 with respect to the humerus 50, such as during a robotic procedure.

Optionally, the first portion 210 can include a stop 216*a* and a stop 216*b* and the second portion 212 can include a stop 216*c*. The stops 216*a* and 216*b* can be connected to an internal portion or surface of the first portion 210 and the bone spikes 214*a* and 214*b* can extend therefrom. Similarly, the stop 216*c* can be connected to an internal portion of surface of the second portion 212 and the bone spike 214*c* can extend therefrom. The stops 216*a*, 216*b*, and 216*c* can each be engageable with a bone, such as the humerus 50, to help limit penetration of the bone spikes 214*a*, 214*b*, and 214*c*, respectively, into the bone. The use of three bone spikes helps the assembly 200 to be stable and adaptive to a variety of bone morphologies. Three bone spikes also provides three points of contact to help provide good control of all degrees of freedom.

FIGS. 3A-3D also show that the locking device 208 can include retainers 218*a* and 218*b* (collectively referred to as retainers 218), where the retainers 218 can be connected to the second portion 212 such as to form a channel 220 to retain at least a portion of the surgical cable 202 therein. The retainers 218 can help to position the surgical cable 202 near an actuator 224 and lock 226 of the locking device 208. A notch 222 can be in the second portion 212 and can also help to receive and retain the surgical cable 202, such as near the actuator 224 and the lock 226.

The actuator 224 and lock 226 can be connected to the second portion 212. The 224 can be a cam or other rotatable member configured to rotate to cause movement of the lock 226 with respect to the second portion 212 and the surgical cable 202. The lock 226 can be a hex nut or other rigid member engageable with the surgical cable 202, such as to compress the surgical cable 202 against the retainers 218 or other portion of the second portion 212, In operation, the actuator 224 can be rotatable with respect to the surgical cable 202 and the second portion 212 to lock and unlock the surgical cable 202. A quarter turn of the actuator 224 clockwise can move the actuator 224 to the locked position where the 226 engages the surgical cable 202 to compress the surgical cable 202 against the second portion 212. A quarter turn of the actuator 224 counter-clockwise can move the actuator 224 to the unlocked position where the 226 disengages the surgical cable 202 to decompress the surgical cable 202, allowing the surgical cable 202 to be removed. Such a process can be repeatable and reversible and can be performed using a ⅛$^{th}$ rotation, ½ rotation, or the like.

FIGS. 3A-3D also show a guide bore 228*a* and a guide bore 228*b* (collectively referred to as guide bores 228), which can extend through the first portion 210 of the plate 206. The guide bore 228*a* can be located in alignment with the bone spike 214*a*, and the 228*b* can be located in alignment with the bone spike 214*b*. The guide bores 228 can each be configured to receive a drill bit therethrough to create a bore in the bone (e.g., the humerus 50). Following creation of the bore, the bone spike 214*a* and the bone spike 214*b* can be positioned in the bores to help retain the plate 206 with respect to the bone e.g., the humerus 50). Optionally, the guide bores 228 can be angled with respect to the 206 and the bone spikes 214*a* and 214*b* can be angled in an opposite direction. Optionally, the plate 206 can include drill stops 229*a* and 229*b* for the bores 228*a* and 228*b*, respectively. The drill stops 229*a* and 229*b* can be configured to limit a drill depth of the bone bores, such as to avoid entering an intermedullary canal of the bone (e.g., the humerus 50), which can help prevent the bone spikes 214*a* and 214*b* from entering the intermedullary canal and interfering with placement of a humeral implant stem or insertion thereof into the canal.

Figure 3D:
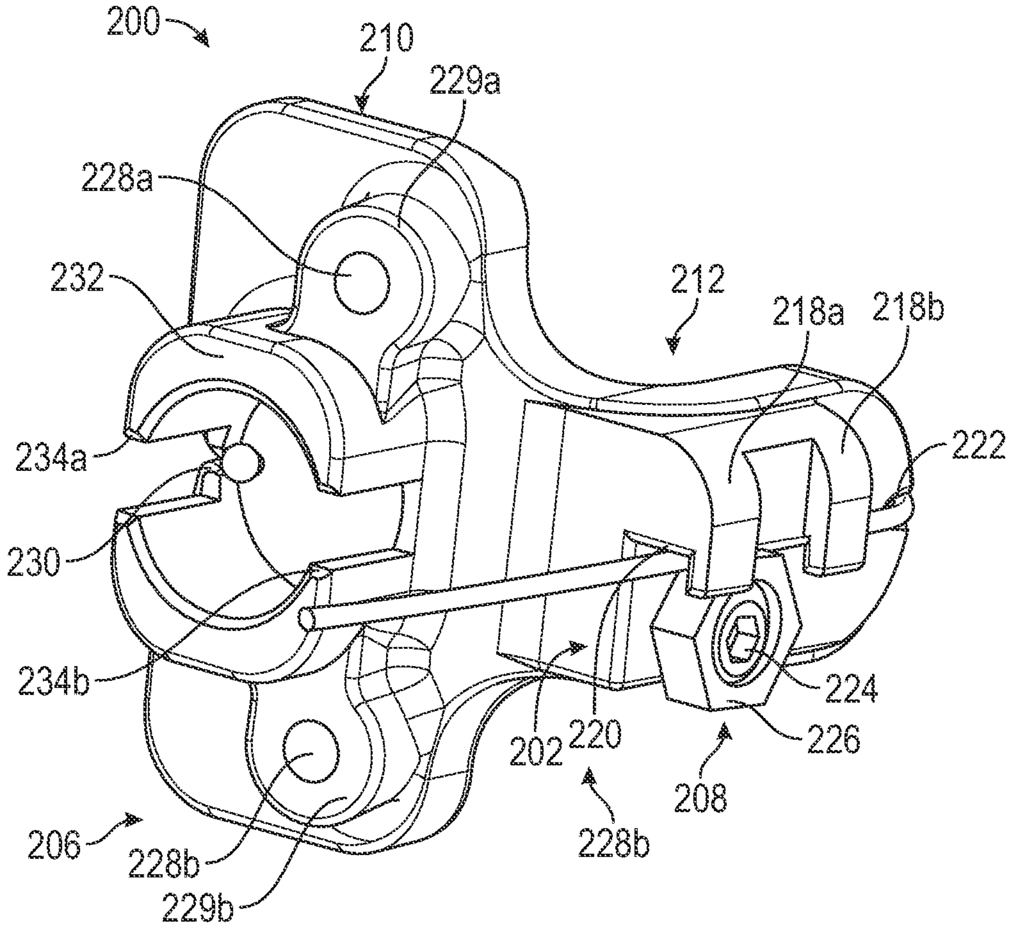
FIG. 3D illustrates an isometric view of a portion of a registration assembly for a robotic surgical system.

FIG. 3D also shows that the plate 206 can include a catch 230 for receiving and retaining at least a portion of the surgical cable 202 to the plate 206. For example, a stopper knot or head of the surgical cable 202 can be retained by the catch 230.

FIGS. 3A and 3D also show that the first portion 210 of the plate 206 can include a collar 232 for receiving and retaining at least a portion of the registration device 204. The collar 232 can include or define one or more alignment slots 234*a* and 234*b* (collectively referred to as alignment slots 234). The alignment slots 234 can each be configured to receive an alignment member 236 of the registration device 204 such as to properly orient the registration device 204 with respect to the plate 206. The collar 232 can also define a bore for receiving and retaining an insert 238 of the registration device 204 for securing the registration device 204 to the plate 206.

FIGS. 4A-4F show a method of using the registration assembly 200. The steps or operations of the method are illustrated in a particular order for convenience and clarity; many of the discussed operations can be performed in a different sequence or in parallel without materially impacting other operations. The method as discussed includes operations performed by multiple different actors, devices, and/or systems. It is understood that subsets of the operations discussed in the method can be attributable to a single actor, device, or system could be considered a separate standalone process or method.

Figures 4A, 4B:
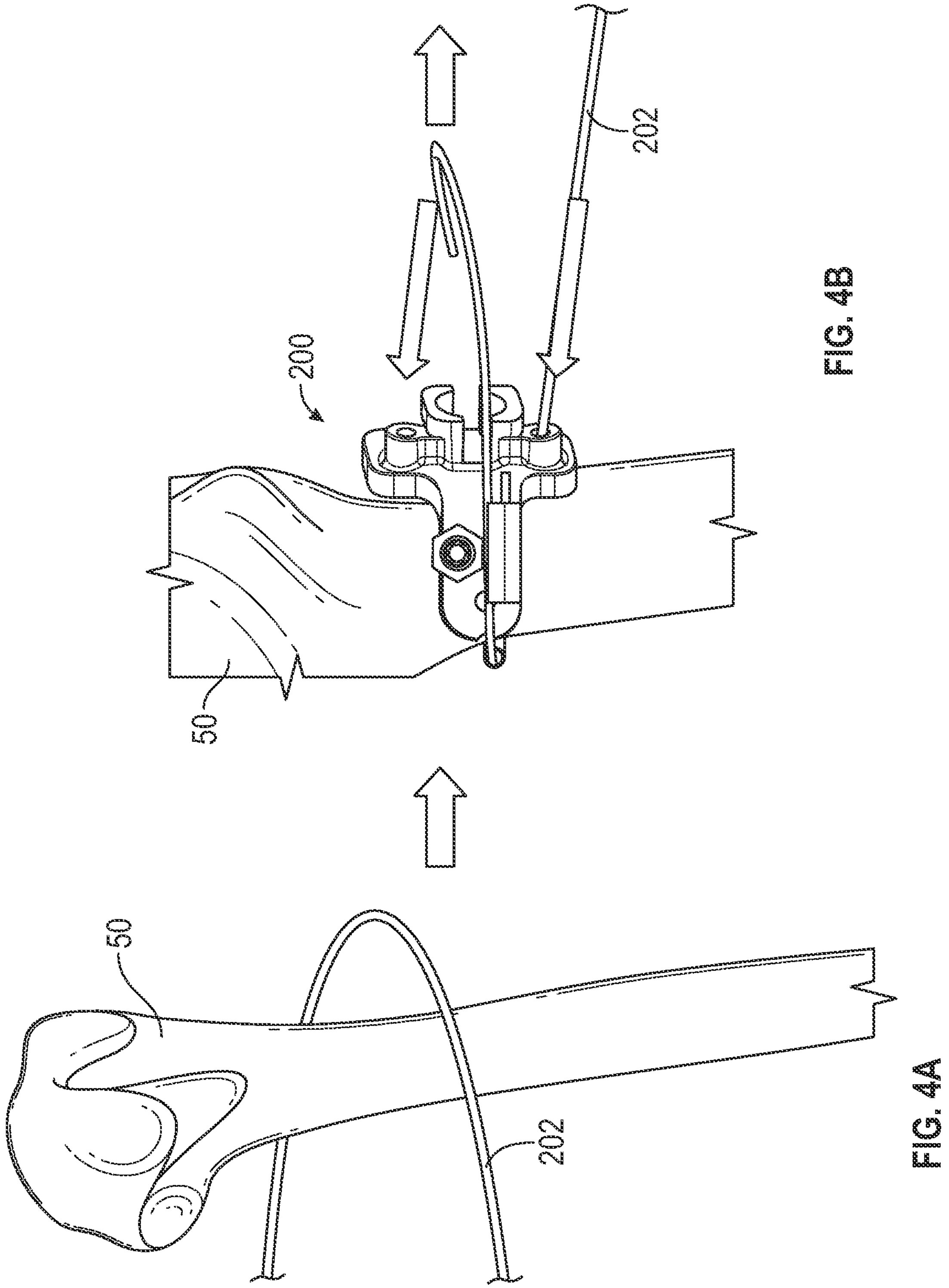
FIG. 4A illustrates a perspective view of a portion of a registration assembly for a robotic surgical system.
FIG. 4B illustrates a perspective view of a portion of a registration assembly for a robotic surgical system.
Figures 4C, 4D:
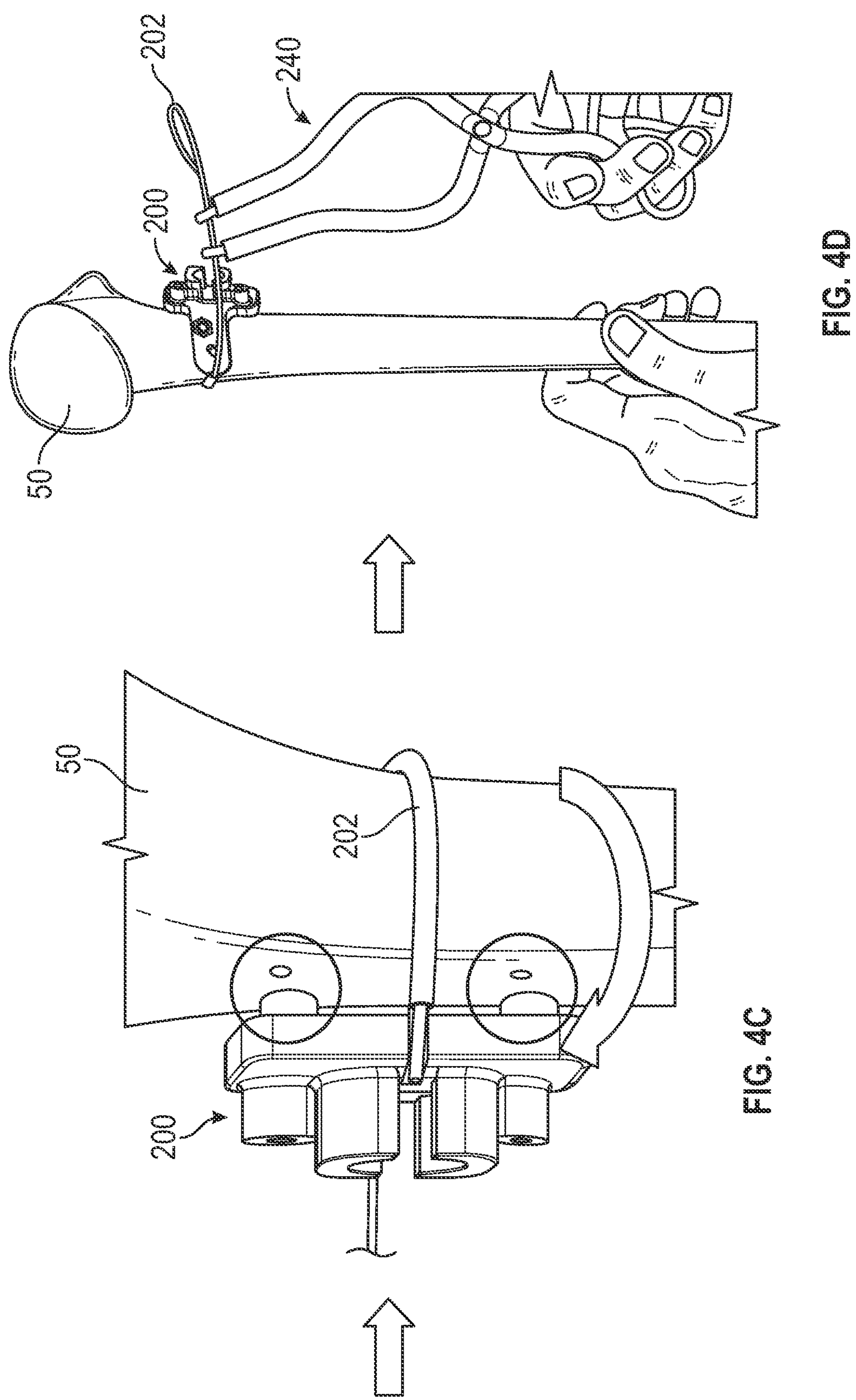
FIG. 4C illustrates a perspective view of a portion of a registration assembly for a robotic surgical system.
FIG. 4D illustrates a perspective view of a portion of a registration assembly for a robotic surgical system.
Figures 4E, 4F:
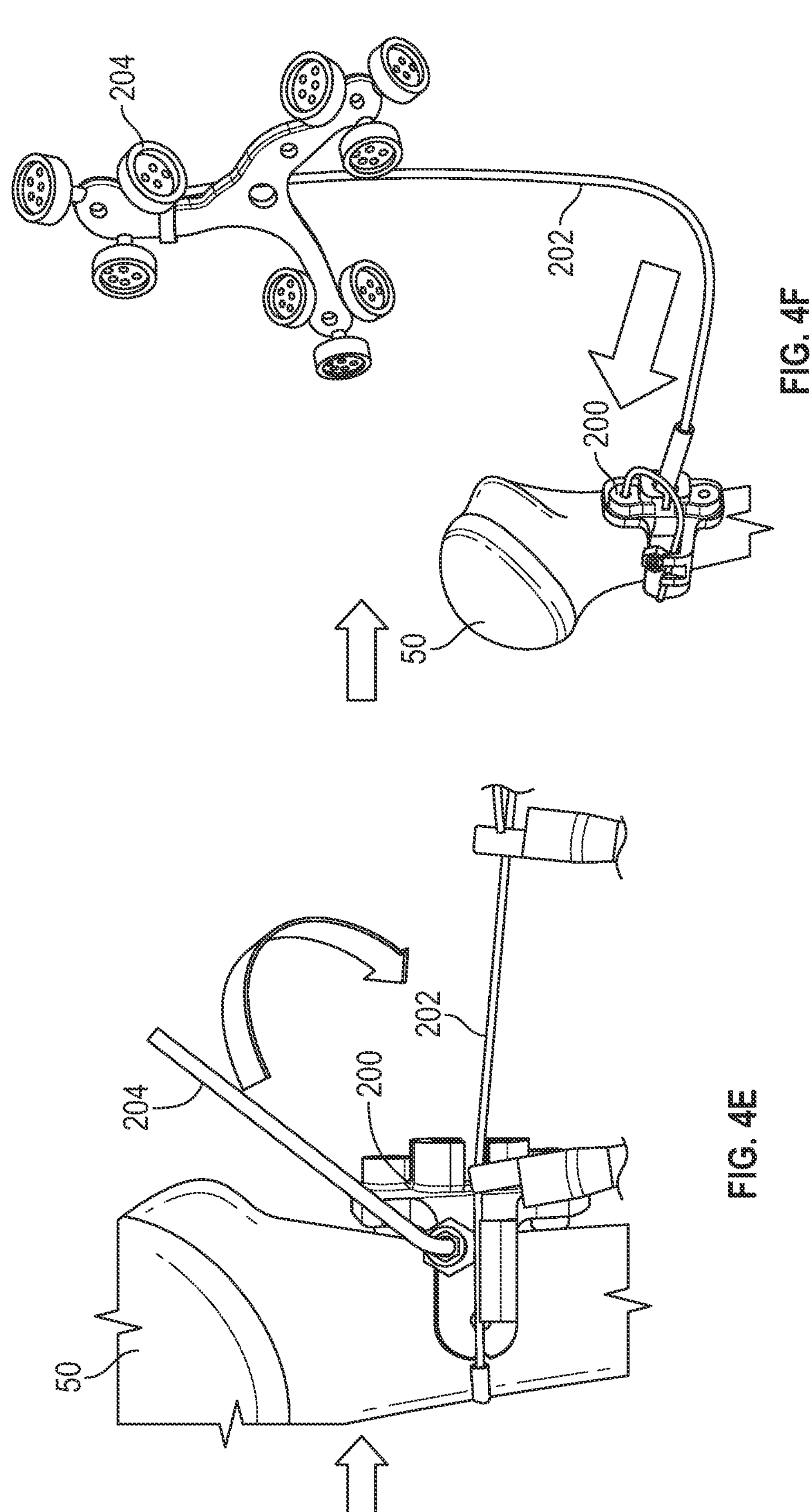
FIG. 4E illustrates a perspective view of a portion of a registration assembly for a robotic surgical system.
FIG. 4F illustrates a perspective view of a portion of a registration assembly for a robotic surgical system.

For example, FIG. 4A shows a humerus 50 on which a surgical procedure can be performed. FIG. 4B shows the surgical cable 202 tightened and secured to the humerus 50 using the locking device 208 to secure the registration assembly 200 thereto. Then, bone bores can be drilled through the guide bores 228. Then, as shown in FIG. 4B, the locking device 208 can be unlocked to allow the bone spikes 214 to be inserted into the bone bores created using the guide bores 228. As shown in FIGS. 4D and 4E a tightening instrument 240, such as a surgical spreader, can be engaged with the locking device 208 and a distal portion of the surgical cable 202 to tension the surgical cable 202 on the humerus 50. Once the surgical cable 202 is tightened to secure the plate 206 to the humerus 50, the registration device 204 can be connected to the plate 206, as shown in FIG. 4F, so that registration can begin, such as using the robotic system 100.

Figure 5A:
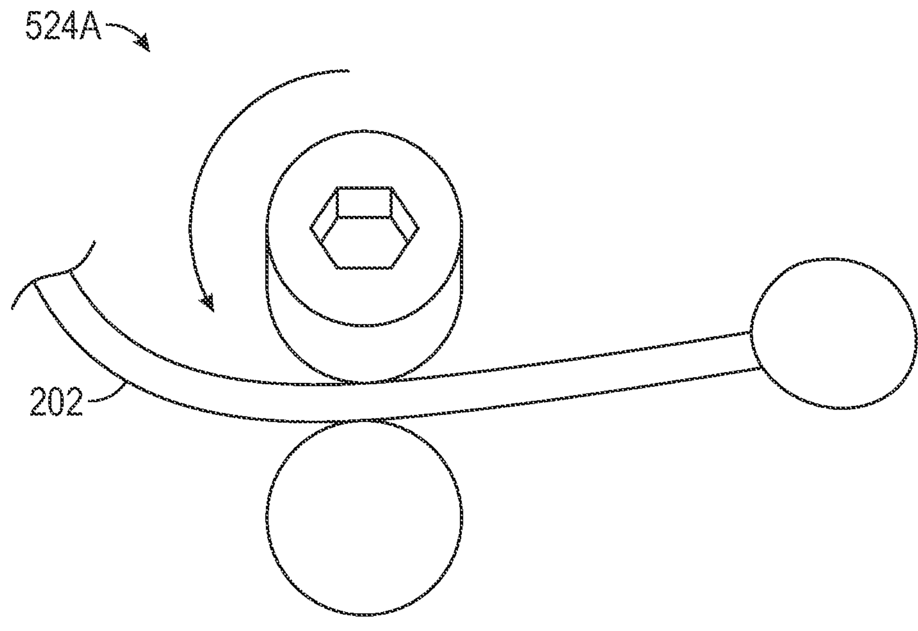
FIG. 5A illustrates a perspective view of a portion of a registration assembly for a robotic surgical system.
Figure 5B:
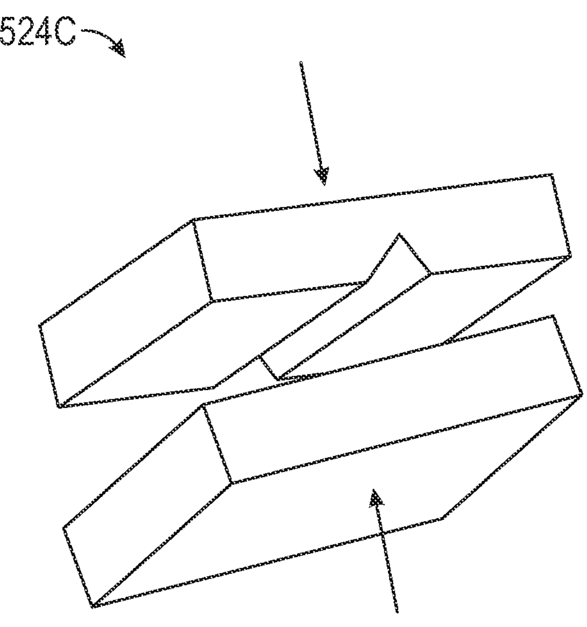
FIG. 5B illustrates a perspective view of a portion of a registration assembly for a robotic surgical system.
Figure 5C:
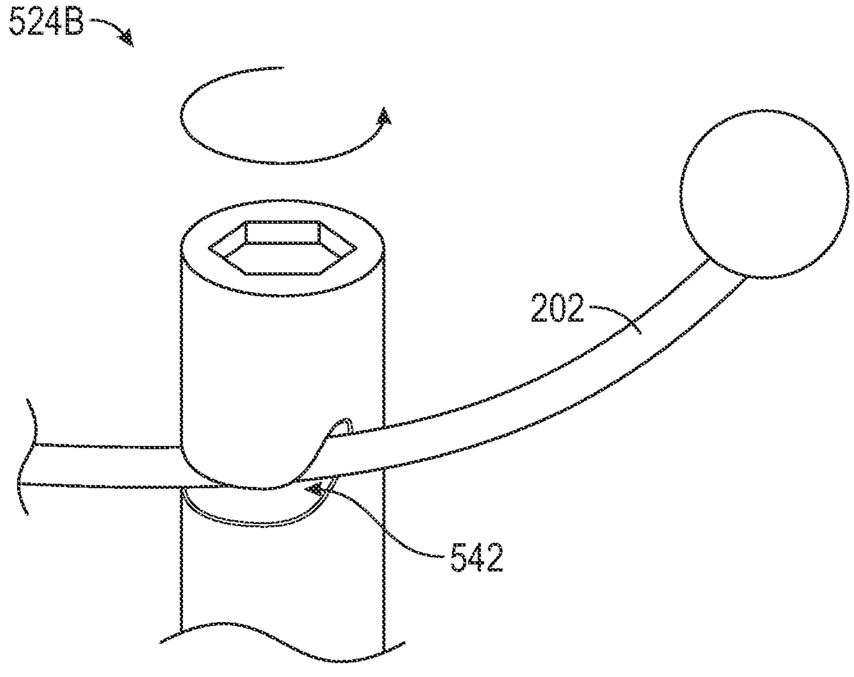
FIG. 5C illustrates a perspective view of a portion of a registration assembly for a robotic surgical system.

FIG. 5A illustrates a perspective view of an actuator 524A of a registration assembly for a robotic surgical system. The actuator 524A can be a cam system that can be used as a part of the locking device 208 of the registration assembly 200. The actuator 524A can be operable to compress the surgical cable 202. FIG. 5B illustrates a perspective view of an actuator 524B of a registration assembly for a robotic surgical system. The actuator 524B can be a clamp system that can be used as a part of the locking device 208 of the registration assembly 200. The actuator 52411 can be operable to compress the surgical cable 202, FIG. 5C illustrates a perspective view of an actuator 524C of a registration assembly for a robotic surgical system. The actuator 524C can be used as a part of the locking device 208 of the registration assembly 200. The actuator 524C can be a rotatable actuator including a cleat 542. The cleat 542 can receive and retain the registration assembly 200 and the actuator 524C rotatable to tighten or tension the surgical cable and to retain the surgical cable 202 to the plate 206.

Figure 6:
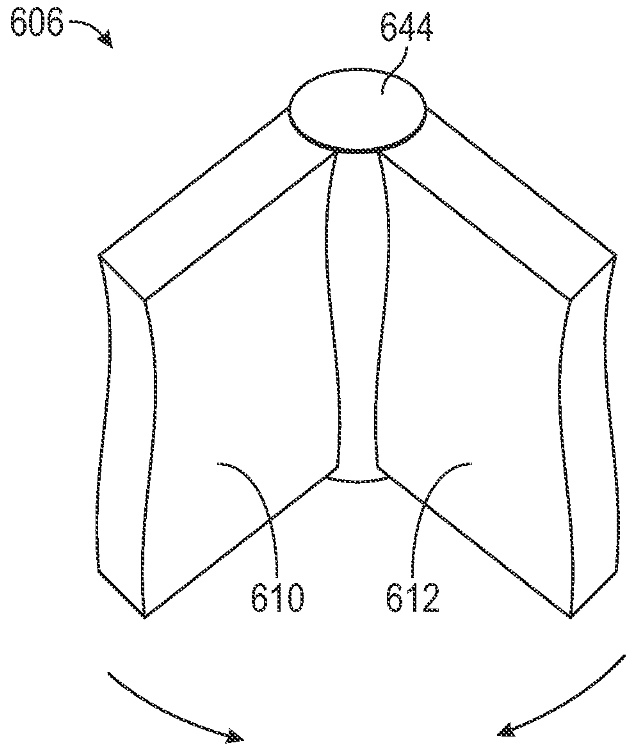
FIG. 6 illustrates a perspective view of a portion of a registration assembly for a robotic surgical system.

FIG. 6 illustrates a perspective view of a plate 606 of a registration assembly for a robotic surgical system. The plate 606 can be used as a part of the registration assembly 200. The plate 606 can include a hinge 644 that can allow a first portion 610 of the plate 606 to rotate with respect to a second portion 612 of the plate 606. Any of the registration assemblies discussed above or below can be modified to include such a hinge.

Figure 7:
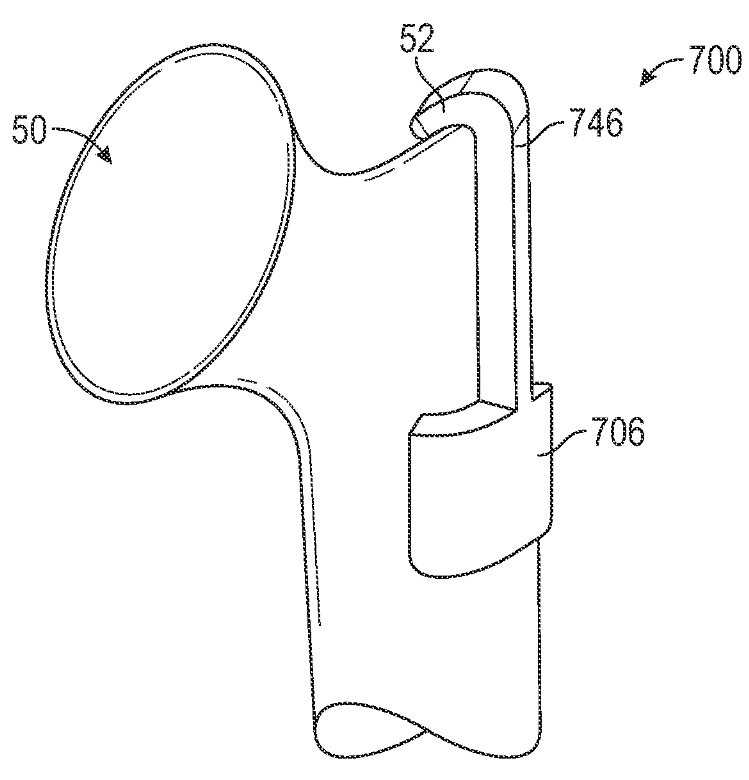
FIG. 7 illustrates a perspective view of a portion of a registration assembly for a robotic surgical system.

FIG. 7 illustrates a perspective view of a portion of a registration assembly 700 for a robotic surgical system that includes an arm 746 connected to a plate 706. The arm 746 can extend from the plate 706 and can be engageable with a tuberosity 52 of the humerus 50 to position or orient the plate 706 with respect to the humerus 50. Any of the registration assemblies discussed above or below can be modified to include such an arm.

Figure 8:
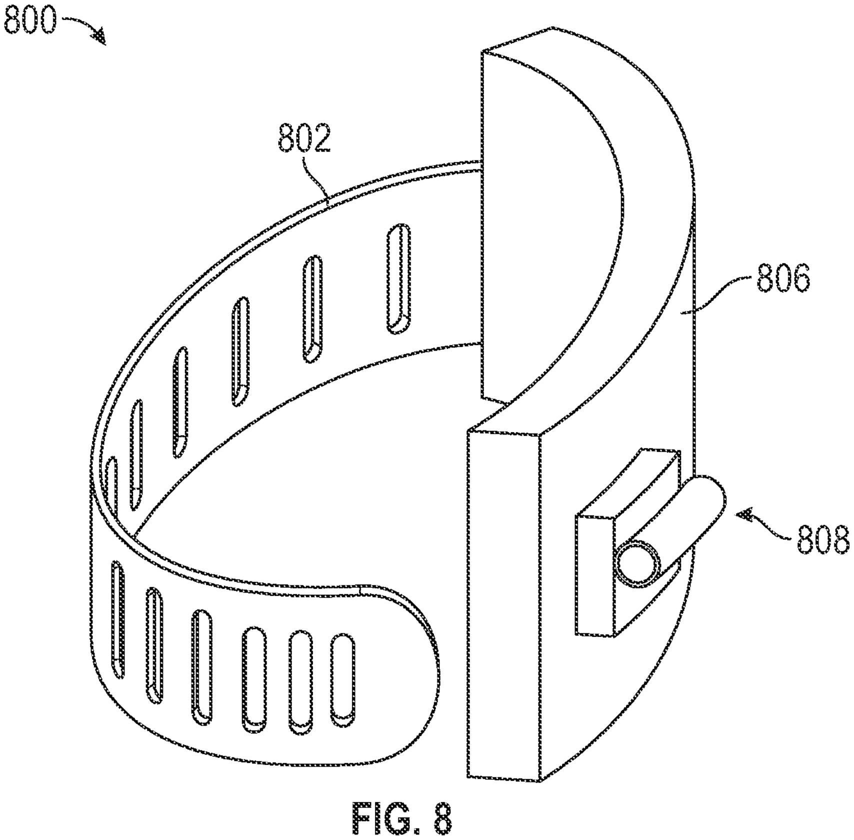
FIG. 8 illustrates a perspective view of a portion of a registration assembly for a robotic surgical system.

FIG. 8 illustrates a perspective view of a portion of a registration assembly 800 for a robotic surgical system. The registration assembly 800 can include a band 802, a plate 806, and a locking device 808. The band 802 and the locking device 808 can form a worm interface operable to loosen and tighten the band 802, such as around a bone. Any of the registration assemblies discussed above or below can be modified to include such a worm interface.

Figure 9:
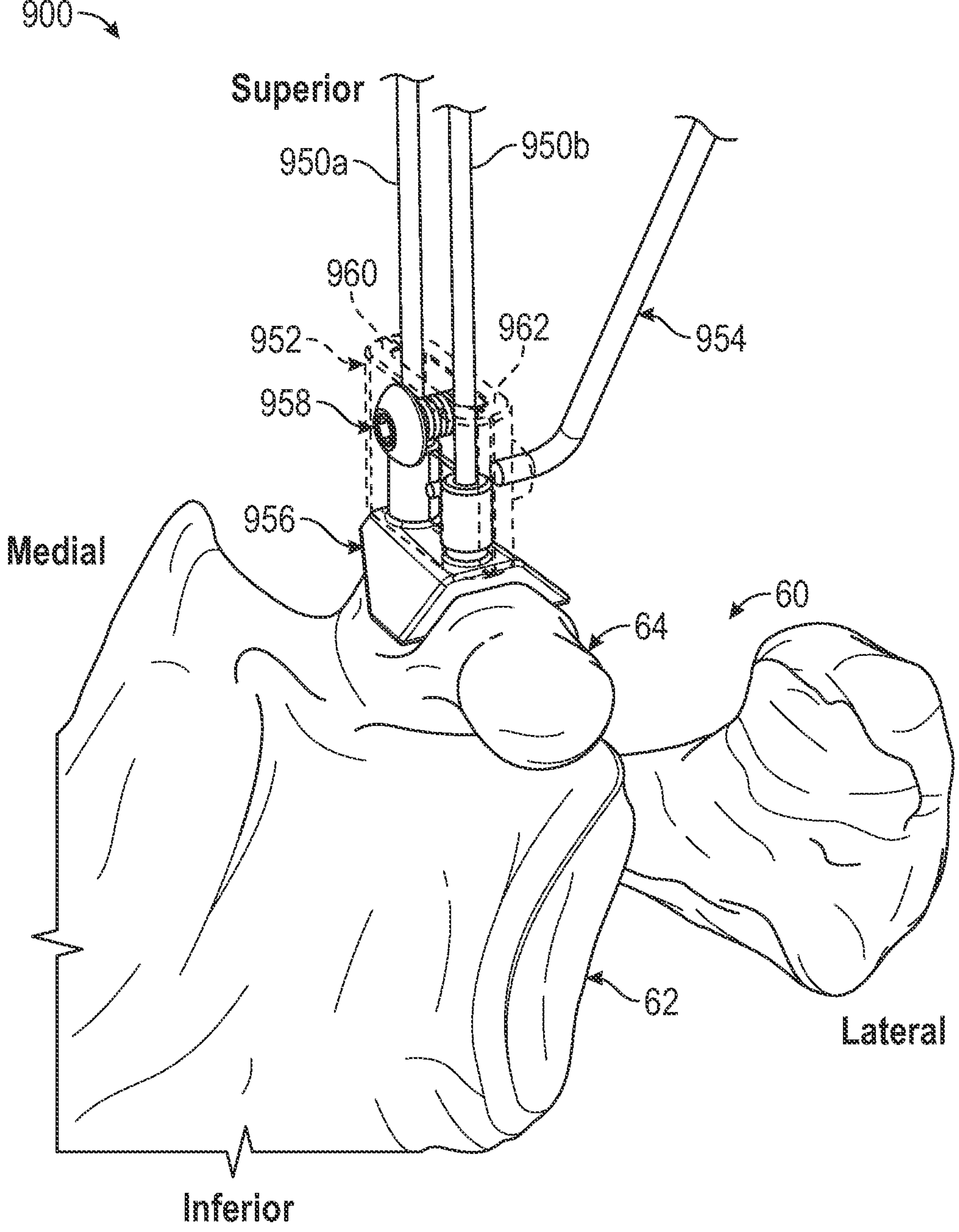
FIG. 9 illustrates an isometric view of a portion of a registration assembly for a robotic surgical system.

FIG. 9 illustrates an isometric view of a portion of a registration assembly 900 for a robotic surgical system. The registration assembly 900 can include a pin 950*a* a pin 950*b* (collectively referred to as pins 950), a housing 952, a registration device 954, a plate 956, and a locking device 958. FIG. 9 also shows a scapula 60, including a glenoid 62, and a coracoid, and shows orientation indicators Superior, Inferior, Medial, and Lateral.

The pins 950, the housing 952, and the plate 956 can each be made of one or more of metals, polymers, or the like, and can be optionally made of biocompatible materials (e.g., titanium or cobalt chromium). The pins 950 can each be elongate members including a sharp or pointed end that can be configured for insertion into bone, such as the coracoid 64 of the scapula 60. The plate 956 can be engageable with an outer surface of the coracoid 64. As discussed in further detail below with respect to FIGS. 10A-11D, the pins 950, the housing 952, and the plate 956 can together be configured to connect the registration device 954 to the coracoid 64 for registration of the registration device 954 and the scapula 60 (including the glenoid 62), such as with the robotic system 100.

Figure 10A:
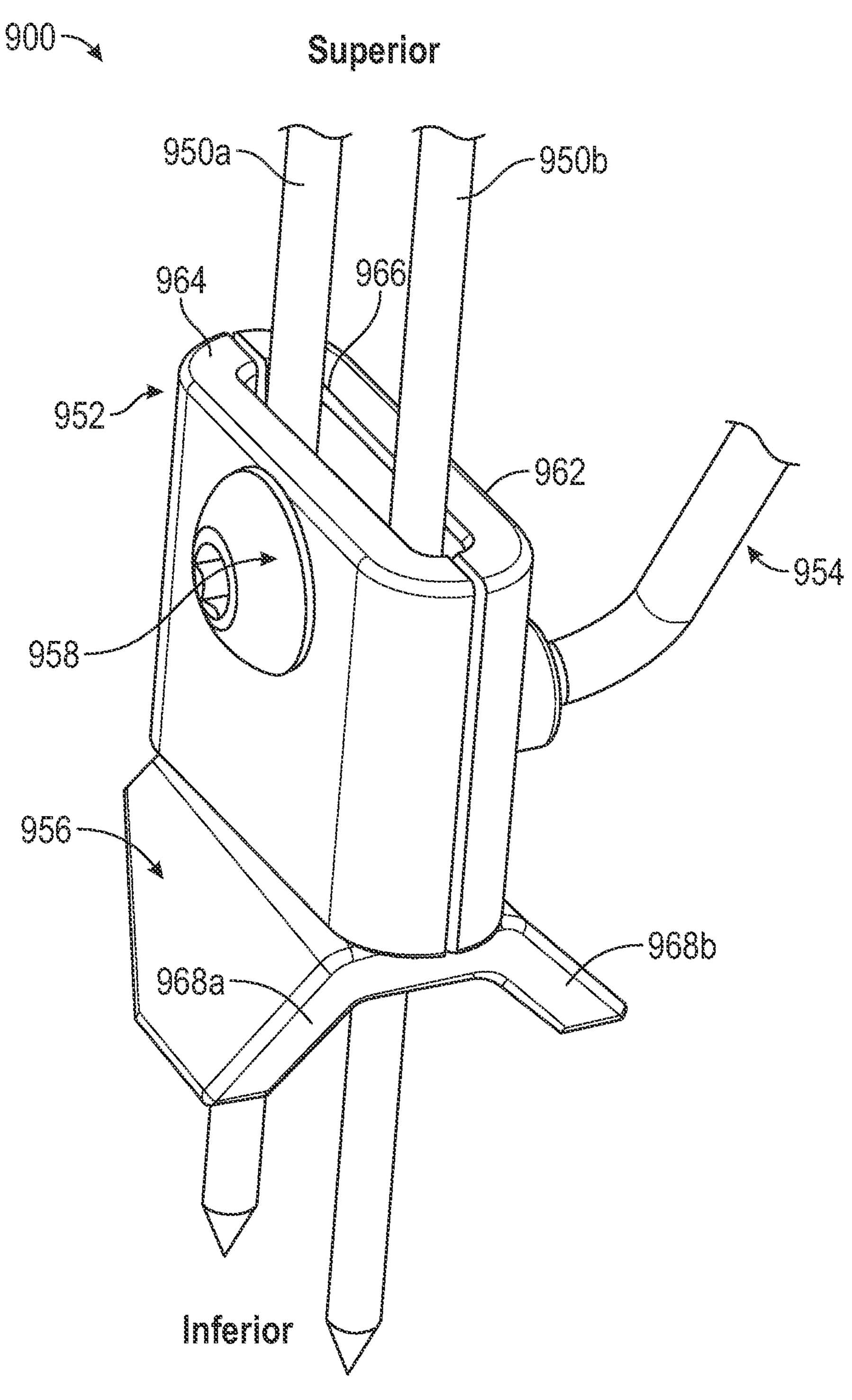
FIG. 10A illustrates an isometric view of a portion of a registration assembly for a robotic surgical system.
Figure 10B:
FIG. 10B illustrates an isometric view of a portion of a registration assembly for a robotic surgical system.
Figure 10B:
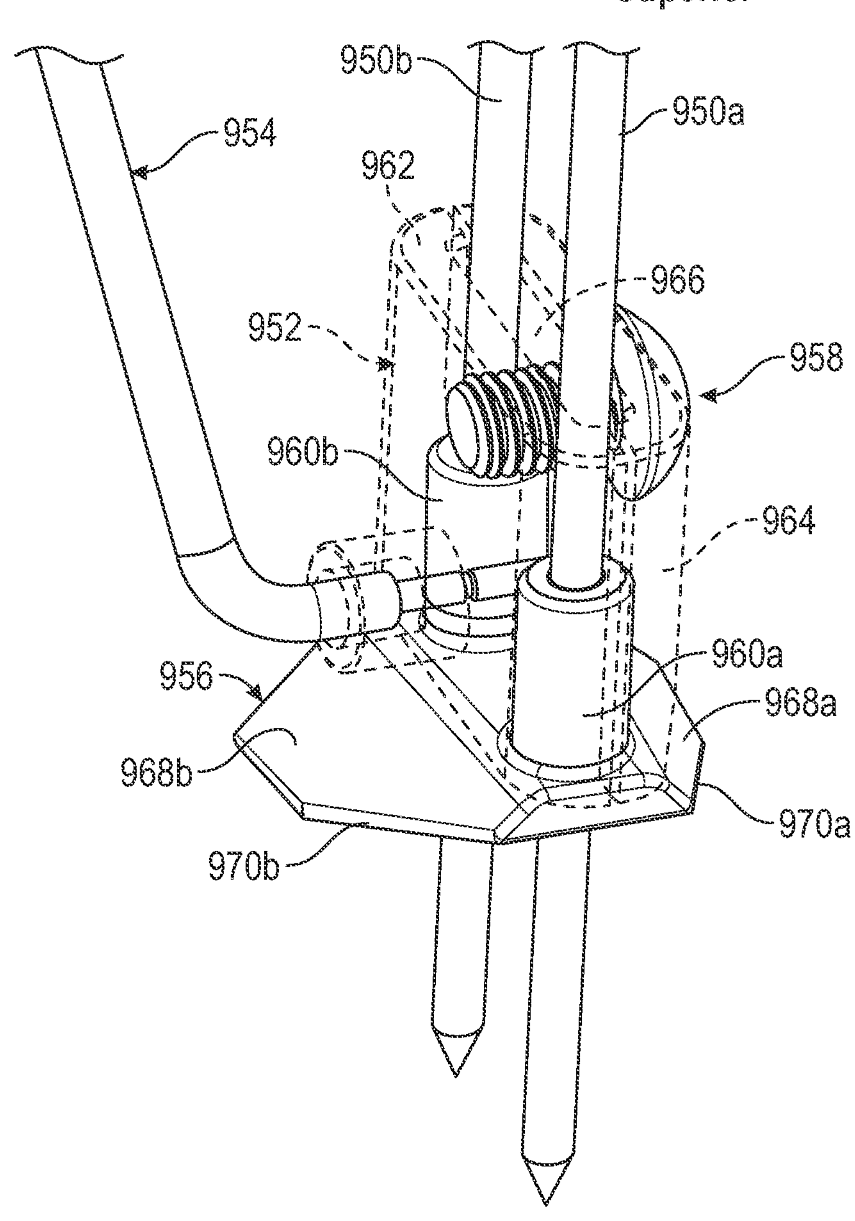

FIG. 10A illustrates an isometric view of the registration assembly 900 for a robotic surgical system. FIG. 10B illustrates an isometric view of a portion of the registration assembly 900 for a robotic surgical system. FIGS. 10A and 10B are discussed together below. FIG. 10B shows the housing 952 in phantom and show orientation indicators Superior and inferior. The registration assembly 900 of FIGS. 10A and 10B can be consistent with the registration assembly 900 of FIG. 9; FIGS. 10A and 10B show additional details of the registration assembly 900. For example, FIGS. 10A and 10B show that the plate 956 can include a collar 960*a* and a collar 960*b* (collectively referred to as collars 960).

The collars 960 can each be connected to, and can extend from, the plate 956. The collars 960 can each define a bore extending therethrough configured to receive the pins 950 therethrough, respectively, such that the pins 950 can extend through the plate 956 to be insertable into the coracoid 64. The collars 960 can also optionally be used as a drill guide to guide a drill bit therethrough, such as for creation of bores in the coracoid 64 for receipt of the pins 950 therein.

FIGS. 10A and 10B also show that the housing 952 can include a first housing member 962 and a second housing member 964, which can be plates or the like. The housing members 962 and 964 can each be engageable with the plate 956 and can together define a housing bore 966 through which the pins 950 can extend to extend into the collars 960. FIGS. 10A and 10B also show that the locking device 958 can be a threaded member, such as a screw or bolt, and can be threadably engageable with the housing members 962 and 964, such as threaded bores thereof. The locking device 958 can be operable to cause the first housing member 962 and the second housing member 964 to move relative to each other to reduce a size of the housing bore 966 to cause the housing members 962 and 964 to engage and clamp the pins 950 to secure the first housing member 962, the second housing member 964, and the plate to the pins, such as to allow the registration device 954 and the scapula 60 to be registered by the robotic system 100.

The registration device 954 can be a component of an optical tracking system such as the tracking system 111, and can function to create a virtual three-dimensional coordinate system within the surgical field for tracking patient anatomy, surgical instruments The registration device 954 can include multiple IR reflective tracking spheres, or similar optically tracked marker devices. The registration device 954 can be connectable to the first housing member 962 and configured to interface with the robotic system 100 for registration of the plate 956 and the scapula 60.

FIGS. 10A and 10B also show that the plate 956 can include a pair of wings 968*a* and 968*b* connected to opposing sides of the plate 956 and extending inferiorly therefrom. The plate 956 and wings 968 can thereby form a shape configured to engage the coracoid 64 and to help locate, position, or orient the registration assembly 900 with respect to the coracoid 64 and the scapula 60. Similarly, the plate 956 can include first and second notches 970*a* and 970*b* in the wings 968*a* and 968*b*, respectively, where the notches 970 can together be configured to locate, position, or orient the registration assembly 900 with respect to the coracoid 64 and the scapula 60, such as by helping to ensure the plate 956 is not positioned backwards on the coracoid 64.

FIGS. 11A-11E show a method of using then registration assembly 900. The steps or operations of the method are illustrated in a particular order for convenience and clarity; many of the discussed operations can be performed in a different sequence or in parallel without materially impacting other operations. The method as discussed includes operations performed by multiple different actors, devices, and/or systems. It is understood that subsets of the operations discussed in the method can be attributable to a single actor, device, or system could be considered a separate standalone process or method.

Figure 11A:
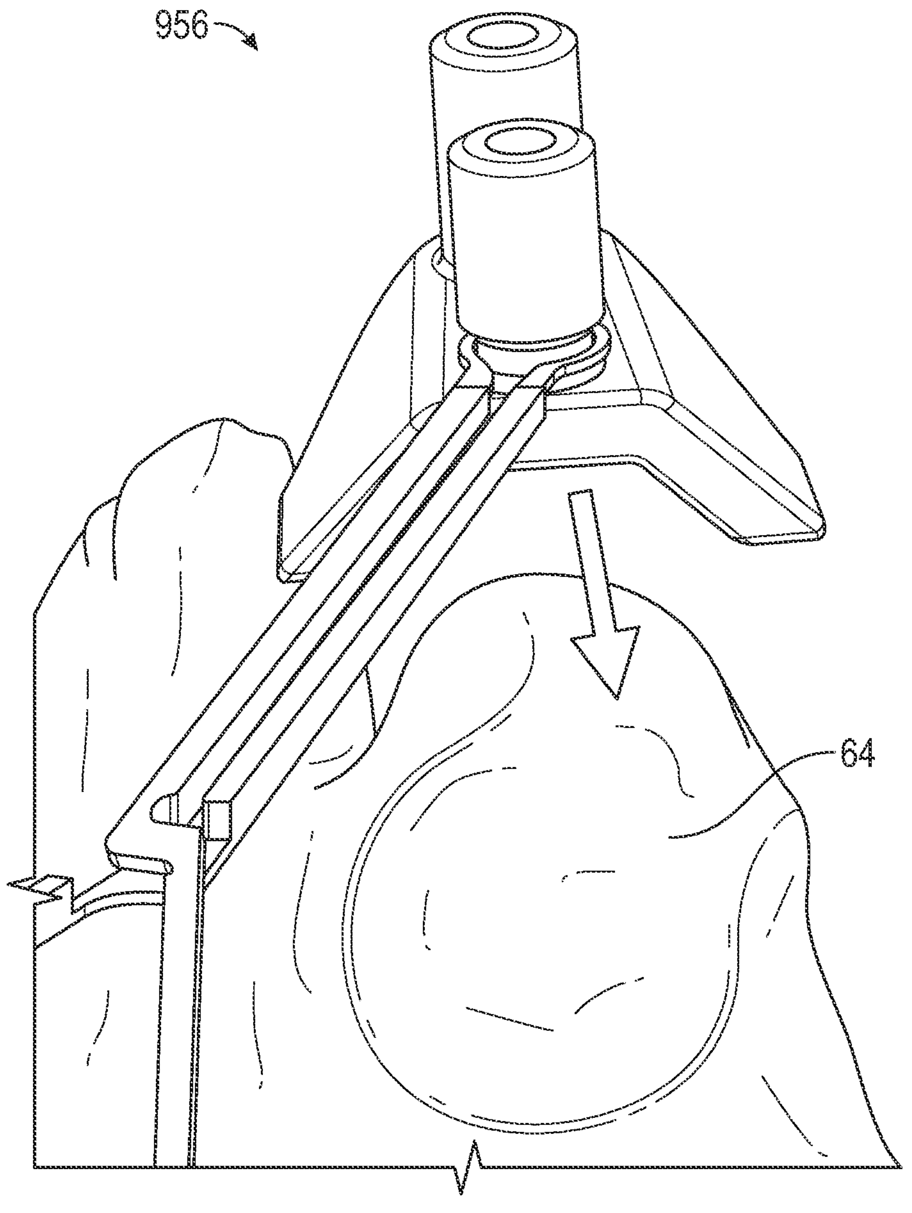
FIG. 11A illustrates a perspective view of a portion of a registration assembly for a robotic surgical system.
Figure 11C:
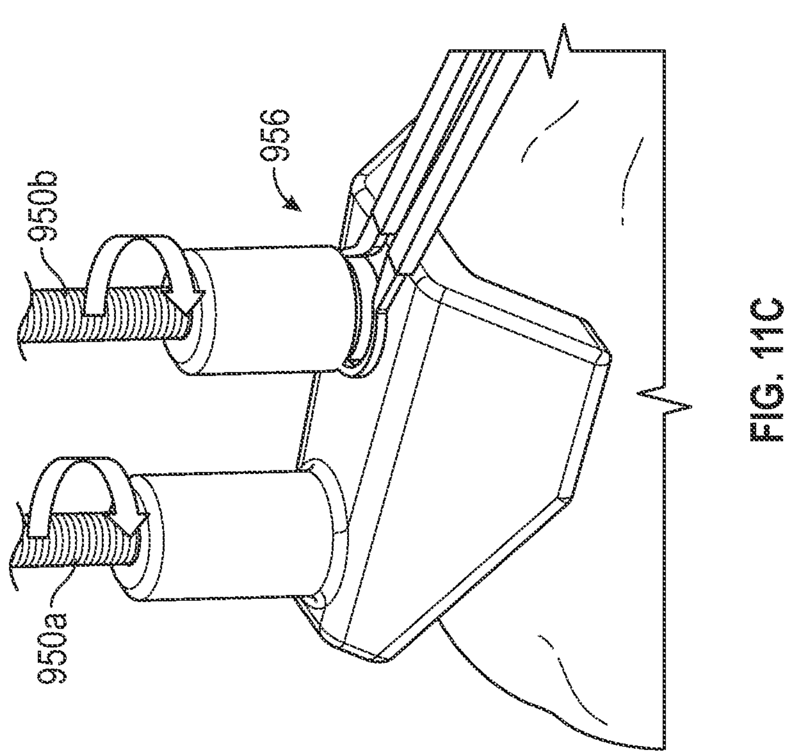
FIG. 11C illustrates a perspective view of a portion of a registration assembly for a robotic surgical system.
Figure 11B:
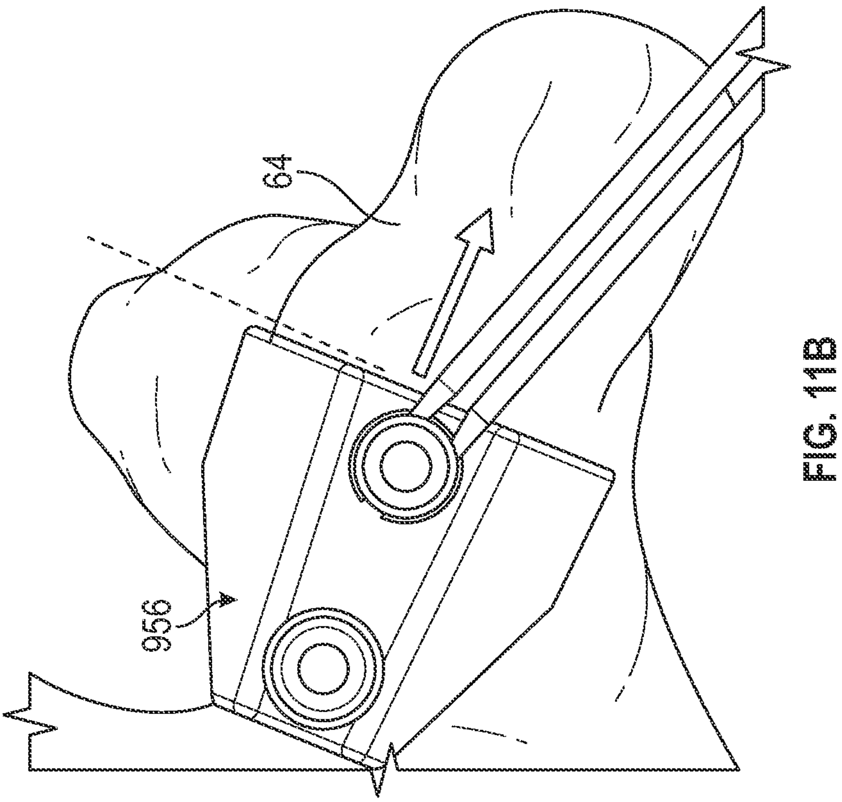
FIG. 11B illustrates a perspective view of a portion of a registration assembly for a robotic surgical system.
Figure 11E:
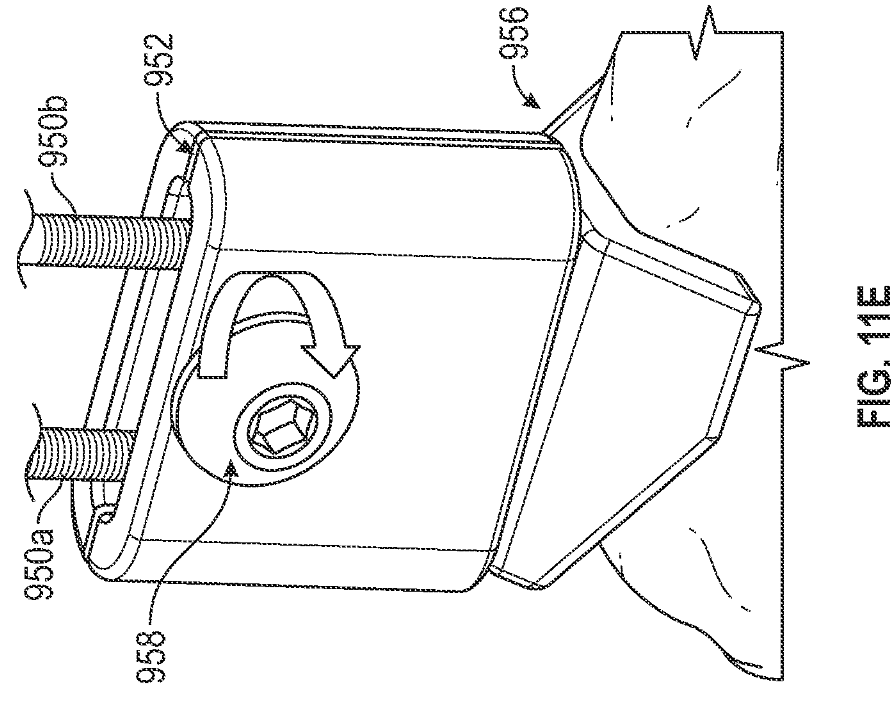
FIG. 11D illustrates a perspective view of a portion of a registration assembly for a robotic surgical system.
FIG. 11F, illustrates a perspective view of a portion of a registration assembly for a robotic surgical system.
Figure 11D:
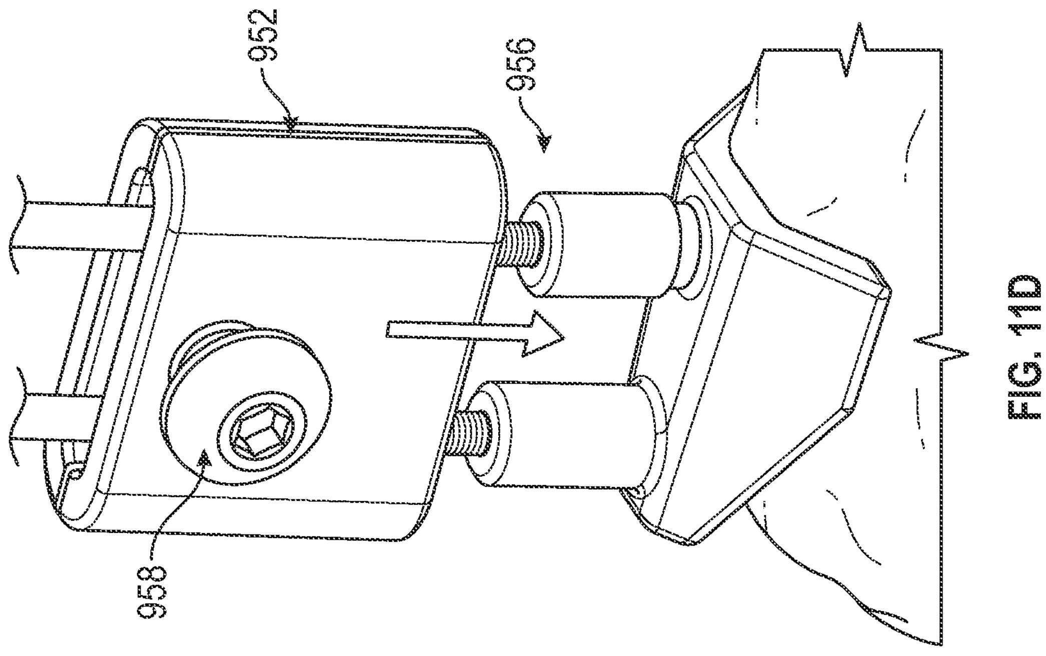

For example, FIG. 11A shows that the plate 956 can be engaged with the coracoid 64. FIG. 11B shows that the plate 956 can be moved laterally until an edge of the plate 956 is aligned with an end of a base of the coracoid 64. FIG. 11C shows that the collars 960 can be used to guide insertion of the pins 950 into the coracoid 64. FIG. 11D shows that the housing 952 can be inserted over the collars 960 to engage a superior portion of the plate 956. The locking device 958 can be operated to reduce an opening size of the housing bore 966 to clamp the housing 952 to the pins 950 to secure the registration assembly 900 to the coracoid 64.

Figure 12A:
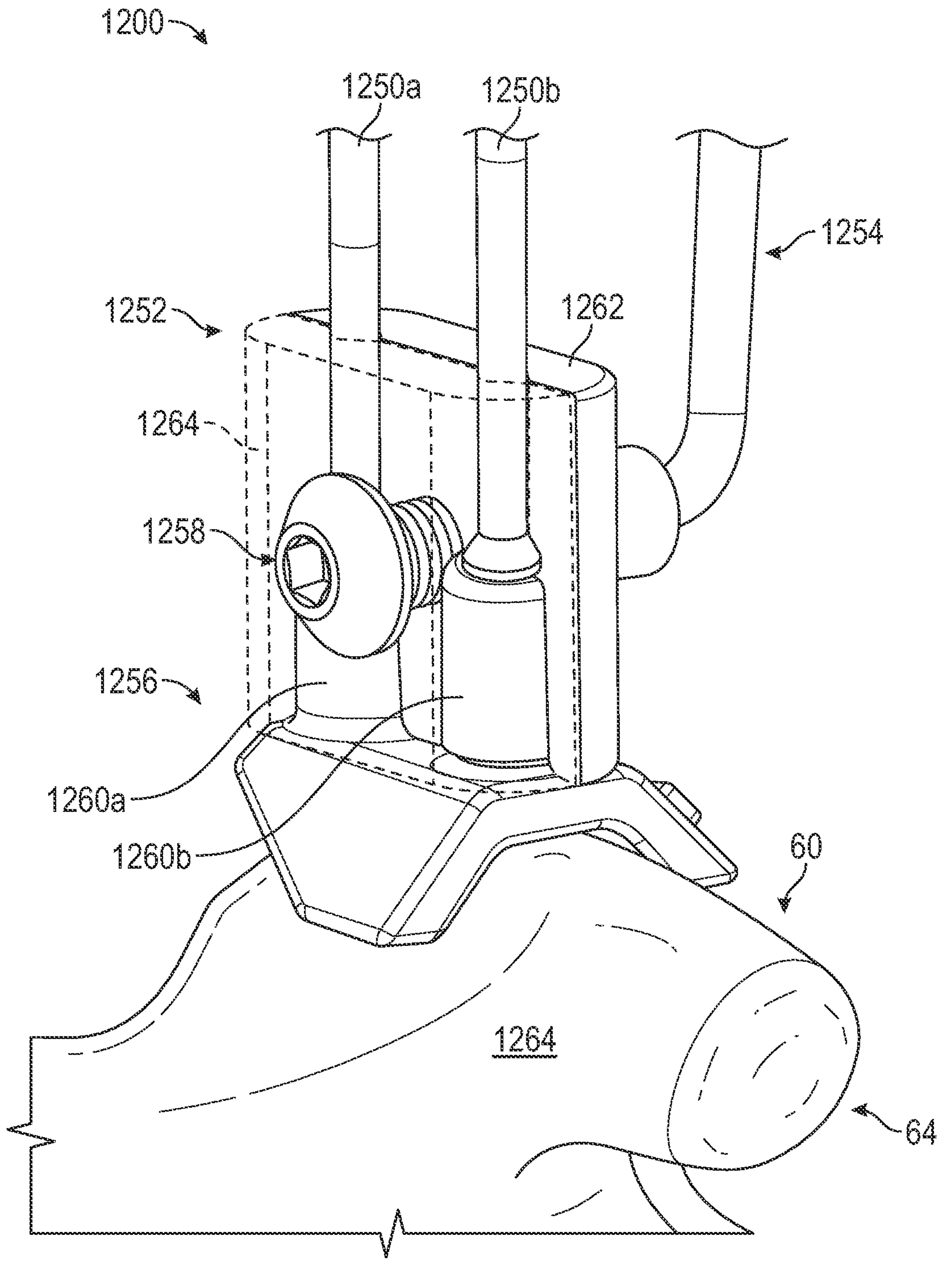
FIG. 12A illustrates a perspective view of a portion of a registration assembly for a robotic surgical system.
Figure 12B:
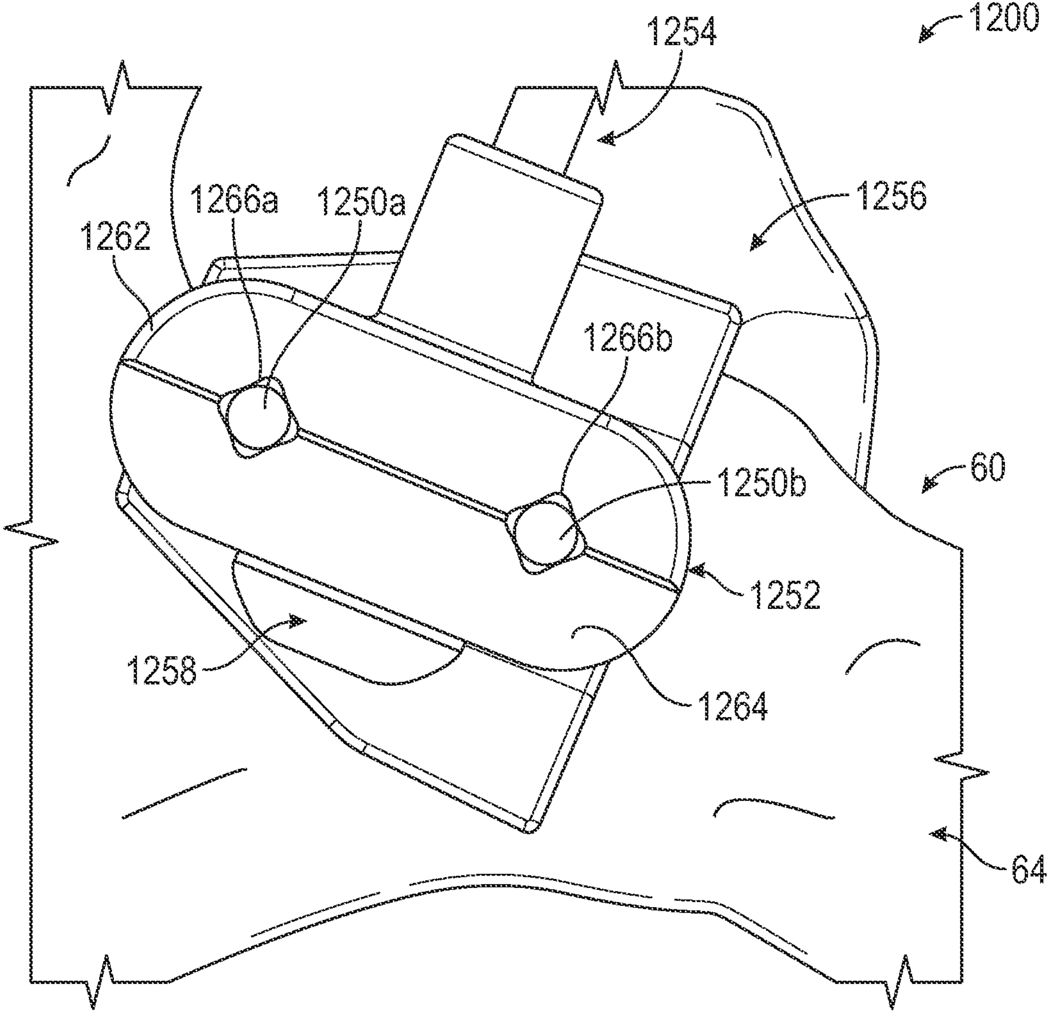
FIG. 12B illustrates a perspective view of a portion of a registration assembly for a robotic surgical system.
Figure 13:
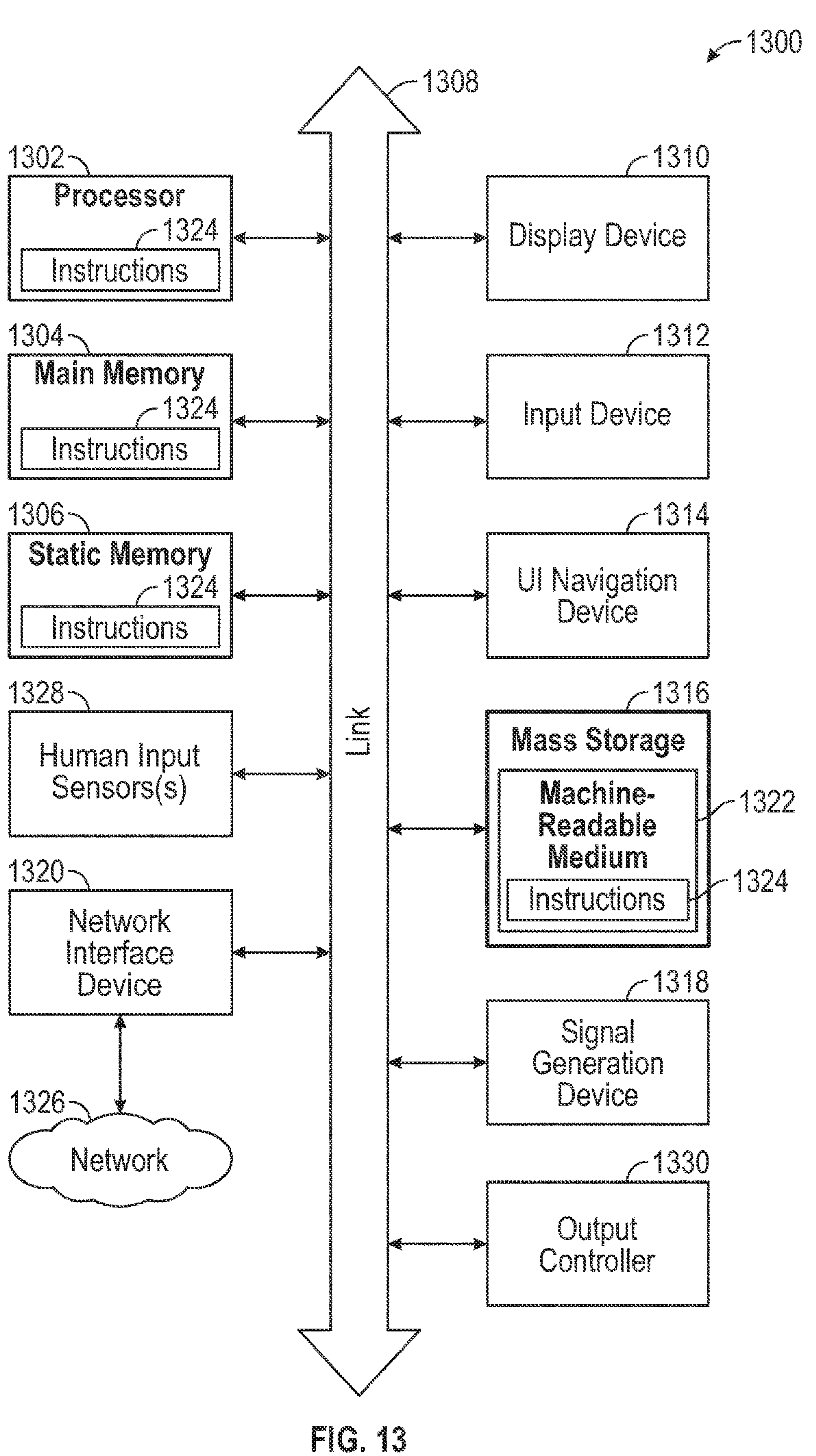
FIG. 13 illustrates a block diagram of an example machine upon which any one or more of the techniques discussed herein can be performed.

FIG. 12A illustrates a perspective view of a portion of a registration assembly 1200 for a robotic surgical system. FIG. 12B illustrates a perspective view of a portion of the registration assembly 1200 for a robotic surgical system including a registration device 1254. FIGS. 12A-12B are discussed together below. The registration assembly 1200 can be similar to the registration assemblies discussed above; the registration assembly 1200 can include a housing that can include separate bores for the pins. Any of the registration assemblies discussed above or below can be modified to include such a housing.

More specifically, a housing 1252 can include a first portion 1262 and a second portion 1264 that can together define a first housing bore 1266*a* and a second housing bore 1266*b* to receive a pair of pins 1250*a* and 1250*b* therethrough, respectively, such as when the pins 1250*a* and 1250*b* are located in collars 1260*a* and 1260*b* of a plate 1256. Operation of a locking mechanism 1258 can reduce a size of the first housing bore 1266*a* and the second housing bore 1266*b* such as to secure the housing 1252 to the pins 1250 to secure the registration assembly 1200 to the scapula 60. Optionally, the first housing bore 1266*a* and the second housing bore 1266*b* can have a square shape, such as to ensure the bores 1266*a* and 1266*b* can engage the pins 1250 regardless of a diameter of the pins 1250. Optionally, the pins 1250 can include depth stops engageable with the collars 1260, respectively, to limit a penetration depth of the pins 1250 into the coracoid 64.

FRI. 13 illustrates a block diagram of an example machine 1300 upon which any one or more of the techniques (e.g., methodologies) discussed herein may perform. Examples, as described herein, may include, or may operate by, logic or a number of components, or mechanisms in the machine 1300. Circuitry (e.g., processing circuitry) is a collection of circuits implemented in tangible entities of the machine 1300 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation.

Accordingly, in an example, the machine readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1300 follow.

In alternative embodiments, the machine 1300 may operate as a standalone device or may be connected (e.g., networked) to other machines. In a networked deployment, the machine 1300 may operate in the capacity of a server machine, a client machine, or both in server-client network environments. In an example, the machine 1300 may act as a peer machine in peer-to-peer (P2P) (or other distributed) network environment. The machine 1300 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1300 may include a hardware processor 1302 (e.g., a central processing unit (CPU), a graphics processing unit (GPU), a hardware processor core, or any combination thereof), a main memory 1304, a static memory (e.g., memory or storage for firmware, microcode, a basic-input-output (BIOS), unified extensible firmware interface (UEFI), etc.) 1306, and mass storage 1308 (e.g., hard drive, tape drive, flash storage, or other block devices) some or all of which may communicate with each other via an interlink (e.g., bus) 1330. The machine 1300 may further include a display unit 1310, an alphanumeric input device 1312 (e.g., a keyboard), and a user interface (UI) navigation device 1314 (e.g., a mouse). In an example, the display unit 1310, input device 1312 and UI navigation device 1314 may be a touch screen display. The machine 1300 may additionally include a storage device (e.g., drive unit) 1308, a signal generation device 1318 (e.g., a speaker), a network interface device 1320, and one or more sensors 1316, such as a global positioning system (GPS) sensor, compass, accelerometer, or other sensor. The machine 1300 may include an output controller 1328, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1302, the main memory 1304, the static memory 1306, or the mass storage 1308 may be, or include, a machine readable medium 1322 on which is stored one or more sets of data structures or instructions 1324 (e.g., software) embodying or utilized by any one or more of the techniques or functions described herein. The instructions 1324 may also reside, completely or at least partially, within any of registers of the processor 1302, the main memory 1304, the static memory 1306, or the mass storage 1308 during execution thereof by the machine 1300. In an example, one or any combination of the hardware processor 1302, the main memory 1304, the static memory 1306, or the mass storage 1308 may constitute the machine readable media 1322. While the machine readable medium 1322 is illustrated as a single medium, the term "machine readable medium" may include a single medium or multiple media (e.g., a centralized or distributed database, and/or associated caches and servers) configured to store the one or more instructions 1324.

The term "machine readable medium" may include any medium that is capable of storing, encoding, or carrying instructions for execution by the machine 1300 and that cause the machine 1300 to perform any one or more of the techniques of the present disclosure, or that is capable of storing, encoding or carrying data structures used by or associated with such instructions. Non-limiting machine readable medium examples may include solid-state memories, optical media, magnetic media, and signals (e.g., radio frequency signals, other photon based signals, sound signals, etc.). In an example, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1324 may be further transmitted or received over a communications network 1326 using a transmission medium via the network interface device 1320 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as'Vi-Fit, IEEE 802.16 family of standards known as WiMax®), IEEE 802.15.4 family of standards, peer-to-peer (P2P) networks, among others. In an example, the network interface device 1320 may include one or more physical jacks (e.g., Ethernet, coaxial, or phone jacks) or one or more antennas to connect to the communications network 1326. In an example, the network interface device 1320 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1300, and includes digital or analog communications signals or other intangible medium to facilitate communication of such software. A transmission medium is a machine readable medium.

Figure 14A:
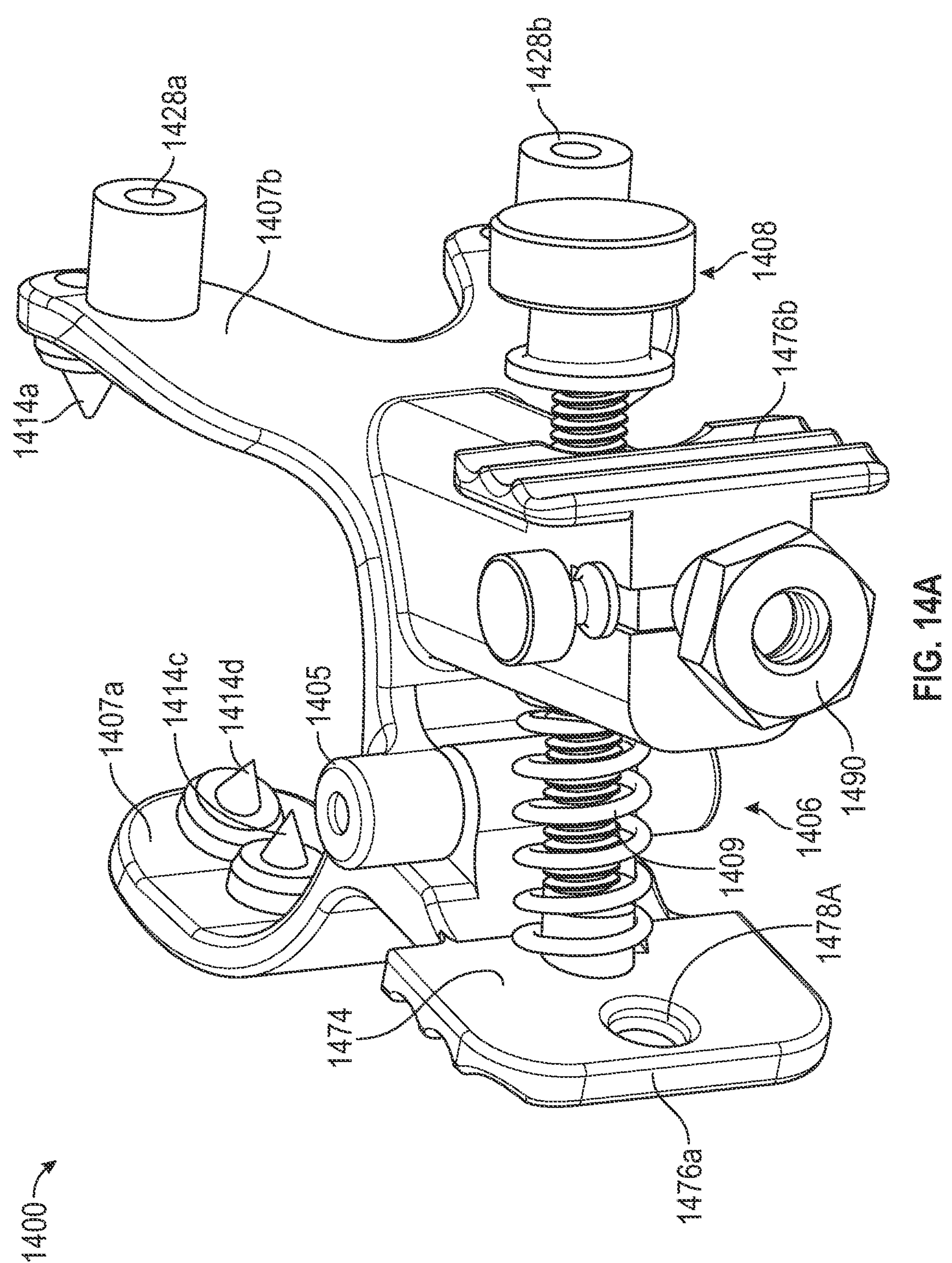
FIG. 14A illustrates an isometric view of a portion of a registration assembly for a robotic surgical system.
Figure 14B:
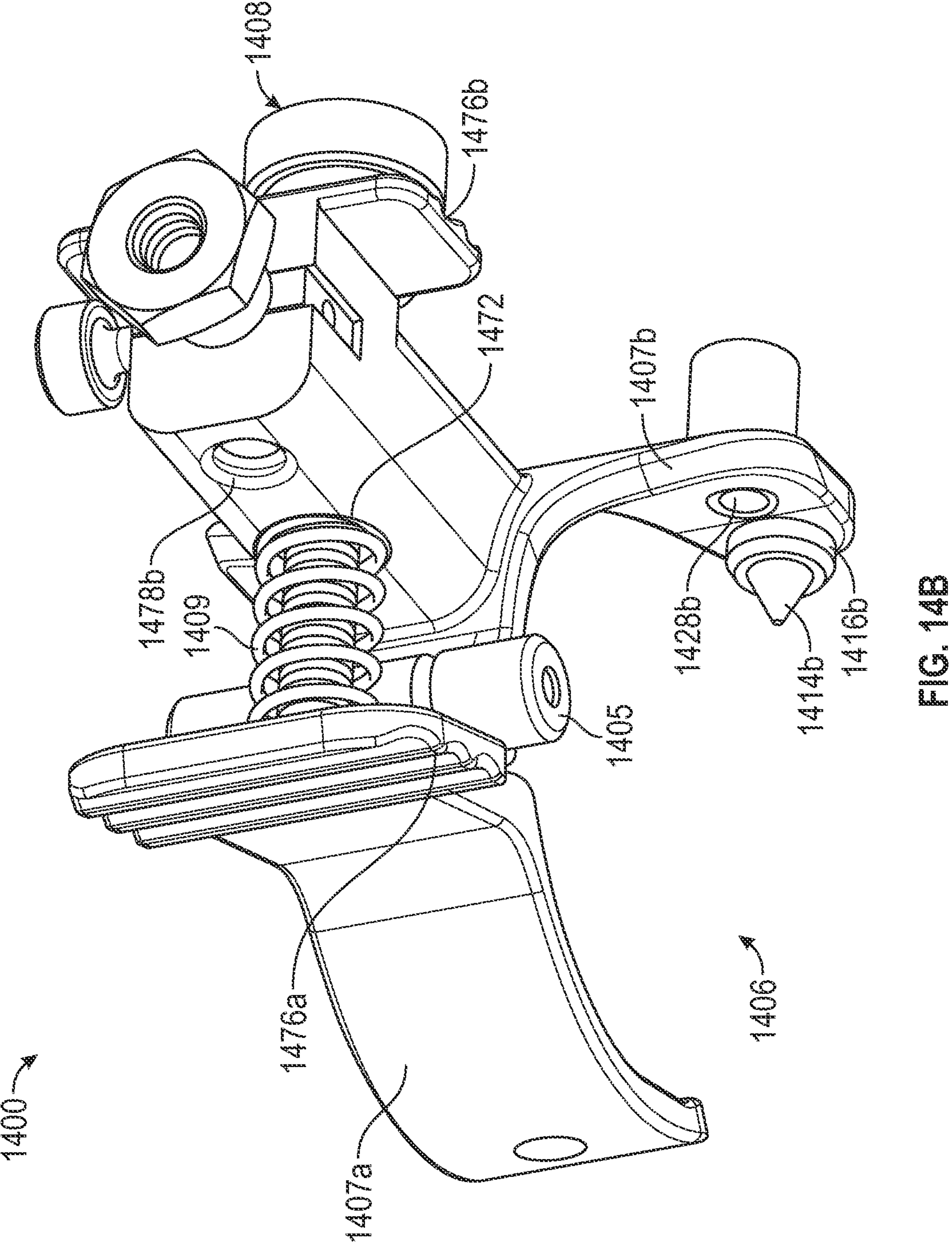
FIG. 14B illustrates an isometric view of a portion of a registration assembly for a robotic surgical system.
Figure 14C:
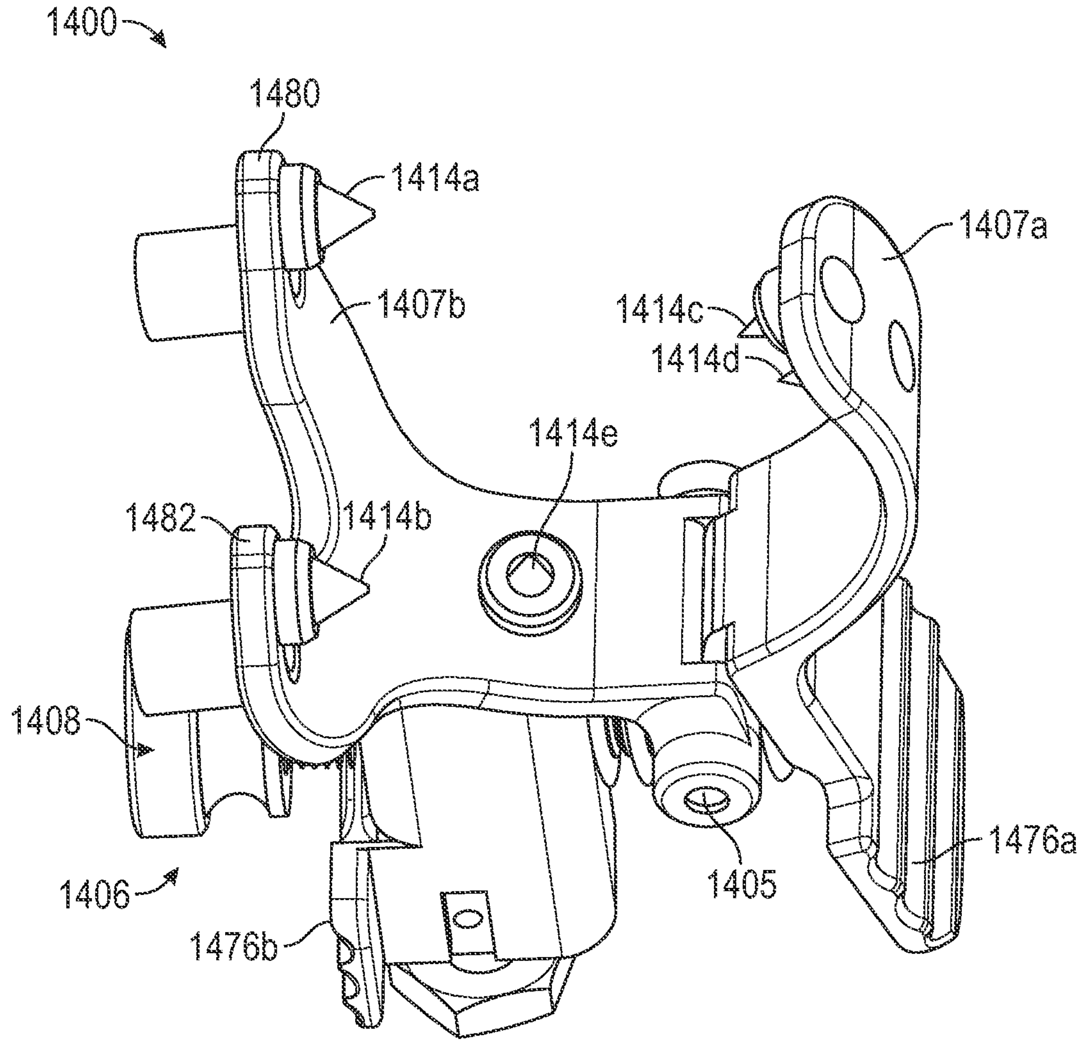
FIG. 14C illustrates an isometric view of a portion of a registration assembly for a robotic surgical system.
Figure 14D:
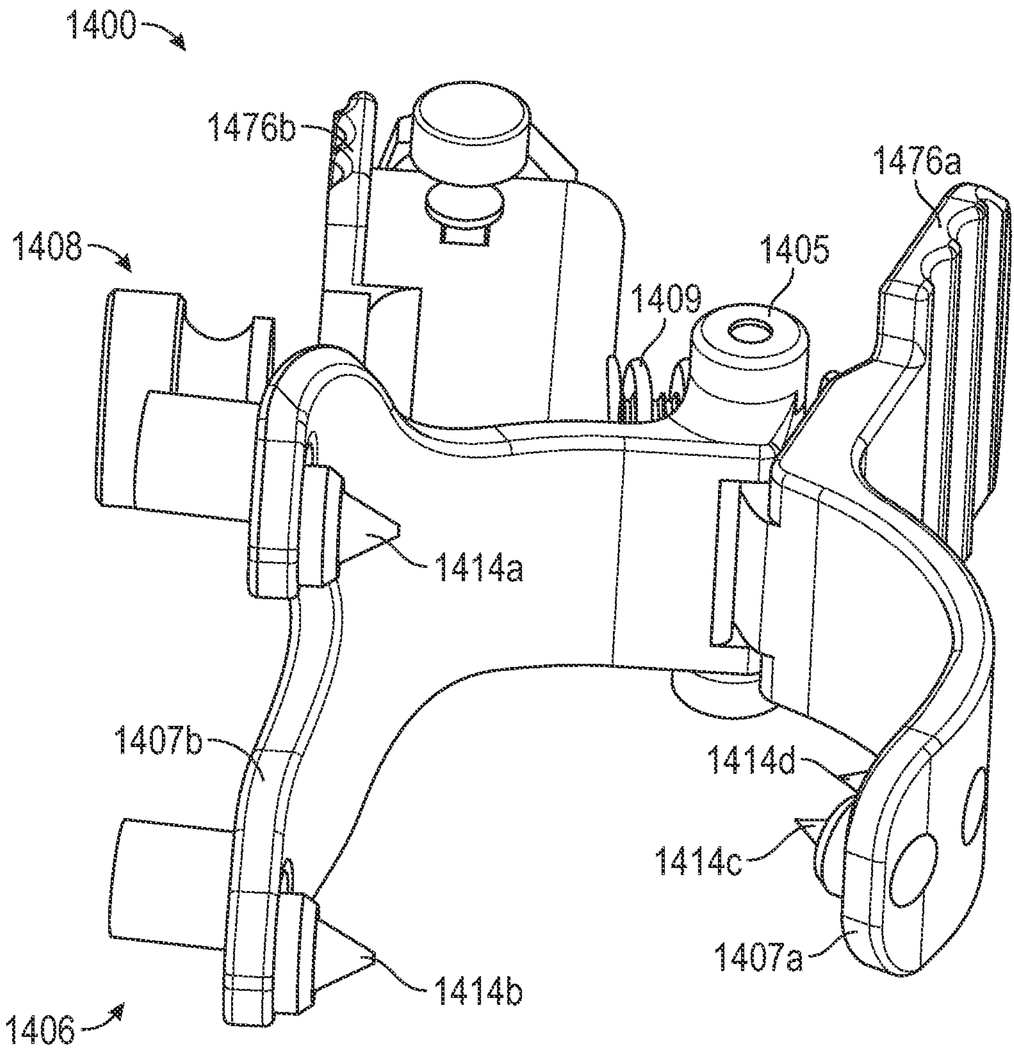
FIG. 14D illustrates an isometric view of a portion of a registration assembly for a robotic surgical system.

FIG. 14A illustrates an isometric view of a portion of a registration assembly 1400 for a robotic surgical system, such as the system 100. FIG. 14B illustrates an isometric view of a portion of the registration assembly 1400 for a robotic surgical system. FIG. 14C illustrates an isometric view of a portion of the registration assembly 1400. FIG. 14D illustrates an isometric view of a portion of the registration assembly 1400. FIGS. 14A-14D are discussed together below. The registration assembly 1400 can be similar to the registration assemblies discussed above; the registration assembly 1400 can include a plate with multiple movable portions. Any of the registration assemblies discussed above or below can be modified to include components of the registration assembly 1400.

The registration assembly 1400 can include a registration device and a plate 1406. A registration device can be a component of an optical tracking system such as the tracking system 111, and can function to create a virtual three-dimensional coordinate system within the surgical field for tracking patient anatomy, surgical instruments. Such a registration device (similar to those discussed above) can be connected to the plate 1406, as described below in further detail.

The plate 1406 can be engageable with an outer surface of a humerus, such as the humerus 50, but can be configured to be engaged with or secured to other bones such as femurs, tibias, or the like. The plate 1406 can be made of one or more of metals, polymers, or the like, and can be optionally made of biocompatible materials (e.g., titanium or cobalt chromium).

The plate 1406 can include a first portion 1407*a* and a second portion 1407*b* that can each be connected to a hinge 1405 such that the first portion 1407*a* and the second portion 1407*b* can be movable with respect to each other and with respect to the hinge 1405 between an open position and a closed position. The first portion 1407*a* can be configured to engage a first portion of the bone and the second portion 1407*b* can be configured to engage a second portion of the bone, such as to clamp onto the bone. The plate 1406 can also include a lock 1408 engageable with one or more of the first portion 1407*a* and the second portion 1407*b* such as to limit movement of the first portion 1407*a* with respect to the second portion 1407*b*. The plate 1406 can also include a biasing element 1409 engaged with one or more of the first portion 1407*a* and the second portion 1407*b* such as to bias the first portion 1407*a* and the second portion 1407*b* toward the closed position.

In operation, the registration assembly 1400 can be secured to the humerus 50 using the first portion 1407*a* and the second portion 1407*b* as a clamp around at least a portion of the bone. Additionally, the plate 1406 can include one or more traction features (e.g., bone spikes) engageable with the humerus 50 to help limit movement of the plate 1406 with respect to the humerus 50. Once the plate 1406 is positioned as desired, the lock 1408 can be operated to fix a position of the first portion 1407*a* and the second portion 1407*b* to help limit movement of the registration assembly 1400 with respect to the bone to help maintain a position of the registration marker or device with respect to the plate 1406 and the bone. Additional details of the registration assembly 1400 are discussed below.

FIGS. 14A and 14B show that the lock 1408 can be a fastener, such as a lead screw or thumb screw 1471, configured to be operated by a user without the use of a tool. The screw 1471 can extend through a bore 1472 of the second portion 1407*b*, which can optionally be a threaded bore. The screw 1471 can also extended into a bore 1474 of the first portion 1407*a*, which can optionally be a threaded bore. Optionally, one of the bore 1472 and the bore 1474 can be a nonthreaded bore configured to capture or retain the screw 1471 to allow threading of the screw 1471 to cause relatively movement of the first portion 1407*a* and the second portion 1407*b* about the hinge 1405.

FIGS. 14A and 14B also show how the hinge 1405 can be formed at least in part by knuckles of the first portion 1407*a* and the second portion 1407*b*. The hinge 1405 can optionally include a hinge pin within a bore of the knuckles. FIGS. 14A and 14B also show that the first portion 1407*a* can include a finger plate 1476*a* and the second portion 1407*b* can include a finger plate 1476*b*. The finger plates 1476 can be engageable by fingers of an operator, such as to move the first portion 1407*a* and the second portion 1407*b* between the open and closed positions when forces applied to the first portion 1407*a* and the second portion 1407*b* overcome forces applied by the biasing element 1409. Optionally, the biasing element 1409 can be omitted. The finger plates 1476 can optionally include ridges, crenulations, fluting, knurling, or other friction features on outer surfaces thereof, such as to improve grip on the finger plates 1476.

FIGS. 14A and 14B also show that the second portion 1407*b* can include guide bores 1428*a* and 1428*b*, which can be similar to those discussed above with respect to the registration assembly 200. FIGS. 14C and 14D show (more clearly) that the first portion 1407*a* can include bone spikes 1414*a* and 1414*b* and the second portion 1407*b* can include bone spikes 1414*c* and 1414*d*. As shown in FIG. 1411, the bone spike 1414*b* can be adjacent or near the guide bore 1428*b* such that after a drill is created in a bone using the guide bore 1428*b*, the bone spikes 1414*b* can be easily moved to be inserted into the bore of the bone. FIG. 14B also shows that the second portion 1407*b* can include a stop 1416*b* to limit a depth of insertion or penetration of the bone spikes 1414*b*. Any of the bone spikes can include such a stop.

FIGS. 14A and 14B also show that the first portion 1407*a* can include a spreader bore 1478*a* extending at least partially into an inner surface of the finger plate 1476*a*. Similarly, the second portion 1407*b* include a spreader bore 1478*b* extending at least partially into an inner surface of the finger plate 1476*b*. The spreader bores 1478 can be configured to receive or retain a surgical spreader therein, such as to allow a spreader to apply outward forces on the finger plate 1476*a* and the finger plate 1476*b*, which can help to move the first portion 1407*a* and the second portion 1407*b* from the closed position to the open position, such as to remove the plate 1406 from the bone. This can be helpful in situations where the bone spikes are secured to a bone and the plate 1406 is difficult to remove by hand from the bone.

FIG. 14C shows that the second portion 1407*b* can include a bone spike 1414*e* ear a center of the plate 1406 (such as between distal tips of the first portion 1407*a* and the second portion 1407*b*). Such a bone spike can help improve friction between the plate 1406 and the bone. Though 4 or 5 bone spikes are shown, 1, 2, 3, 6, 7, 8, 9, 10, or the like bone spikes can be included in the plate 1406. FIG. 14C also shows that the second portion 1407*b* can include multiple fingers 1480 and 1482 which can extend away from the hinge 1405 and can be offset from each other, such as to define a gap therebetween.

FIGS. 14C and 14D also show that the first portion 1407*a* and the second portion 1407*b* can be rounded or curved, such as to match or conform to a shape of a bone. The plate 1406 can be matched to any number of bones such as a femur, humerus, radius, tibia, ulna, rib, clavicle, or the like.

Figure 15:
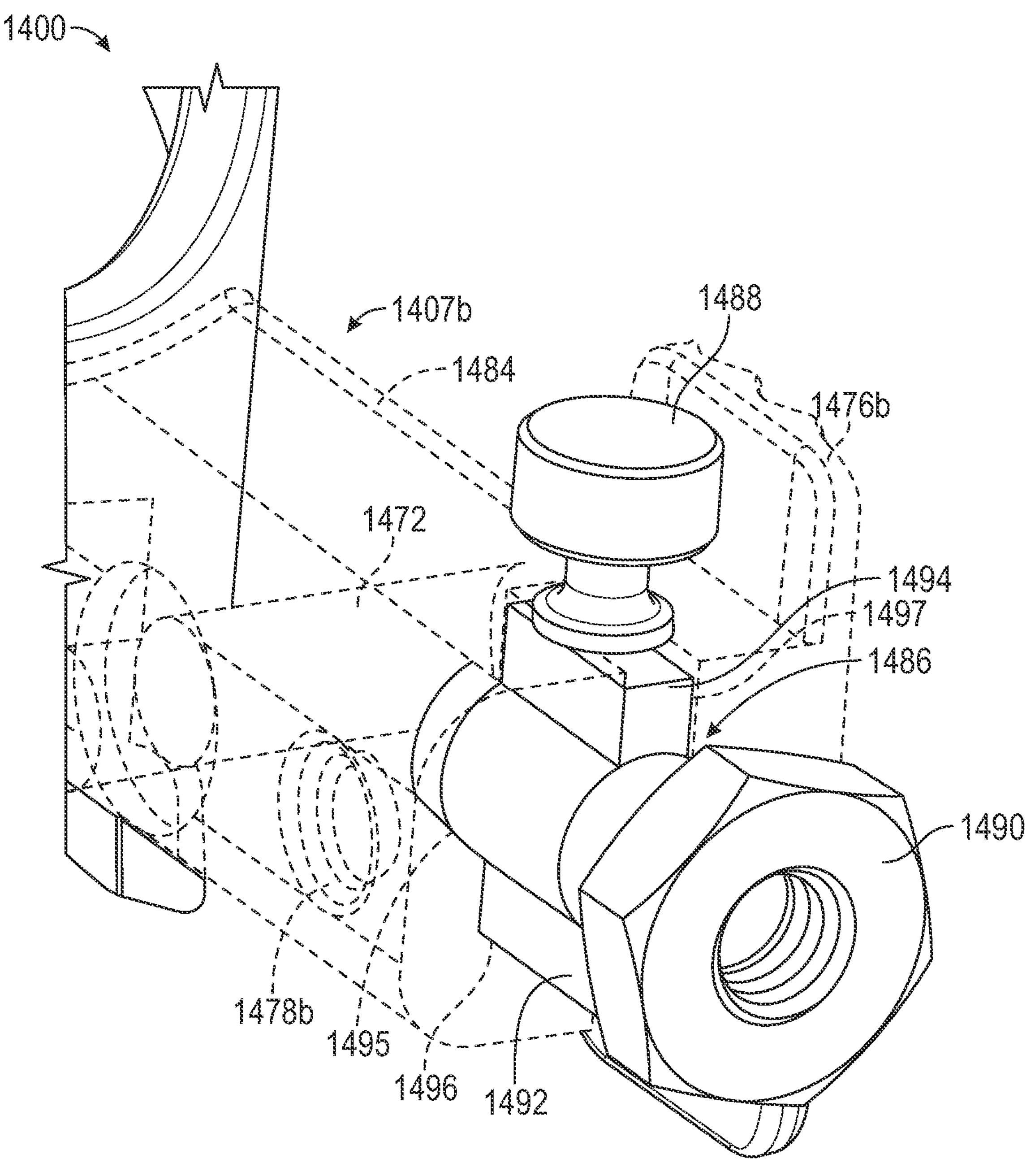
FIG. 15 illustrates an isometric view of a portion of a registration assembly for a robotic surgical system.

FIG. 15 illustrates an isometric view of a portion of the registration assembly 1400. The registration assembly 1400 of FIG. 15 can be consistent with the registration assembly 1400 of FIGS. 14A-14D. FIG. 15 shows additional details of the registration assembly 1400. For example, FIG. 15 shows only the second portion 1407*b*, which can include a support 1484 extending away from a bone engagement portion of the second portion 14076. The support 1484 can include the bore 1472 therethrough and can include the spreader bore 1478*b* therein or thereon. The support 1484 can also be connected to the finger plate 1476*b*.

FIG. 15 also shows that the support 1484 can include a bore or recess to receive a marker coupler 1486. The marker coupler 1486 can include a thumb screw 1488, a retaining nut 1490, and flanges 1492 and 1494. The support 1484 can include a bore 1495 and channels 1496 and 1497. The marker coupler 1486 can be insertable into the bore 1495 of the support 1484 such that the flanges 1492 and 1494 are inserted into the channels 1496 and 1497. Because the flanges 1492 and 1494 can be a prism (such as a portion of a rectangular prism) and the channels 1496 and 1497 can be shaped complimentary to the flanges 1492 and 1494, rotation of the marker coupler 1486 can be limited within the bore 149:5 and with respect to the support 1484 and the second portion 1407*b*. When the marker coupler 1486 is inserted into the support 1484, the thumb screw 1488 can be operated to engage the support 1484 and the flange 1494 to secure the marker coupler 1486 to the support 1484.

The marker coupler 1486 can include a bore for receiving a rod of the marker (such as the rod of the registration device 204). When the rod is inserted into the marker coupler 1486 the retaining nut 1490 can be operated (e.g., rotated) to secure the registration rod and marker to the marker coupler 1486 and therefore to the support 1484, the second portion 1407*b*, and the plate 1406. Such an assembly can allow for relatively quick installation and disassembly, which can help save time during a surgical procedure using the registration assembly 1400.

Figure 16:
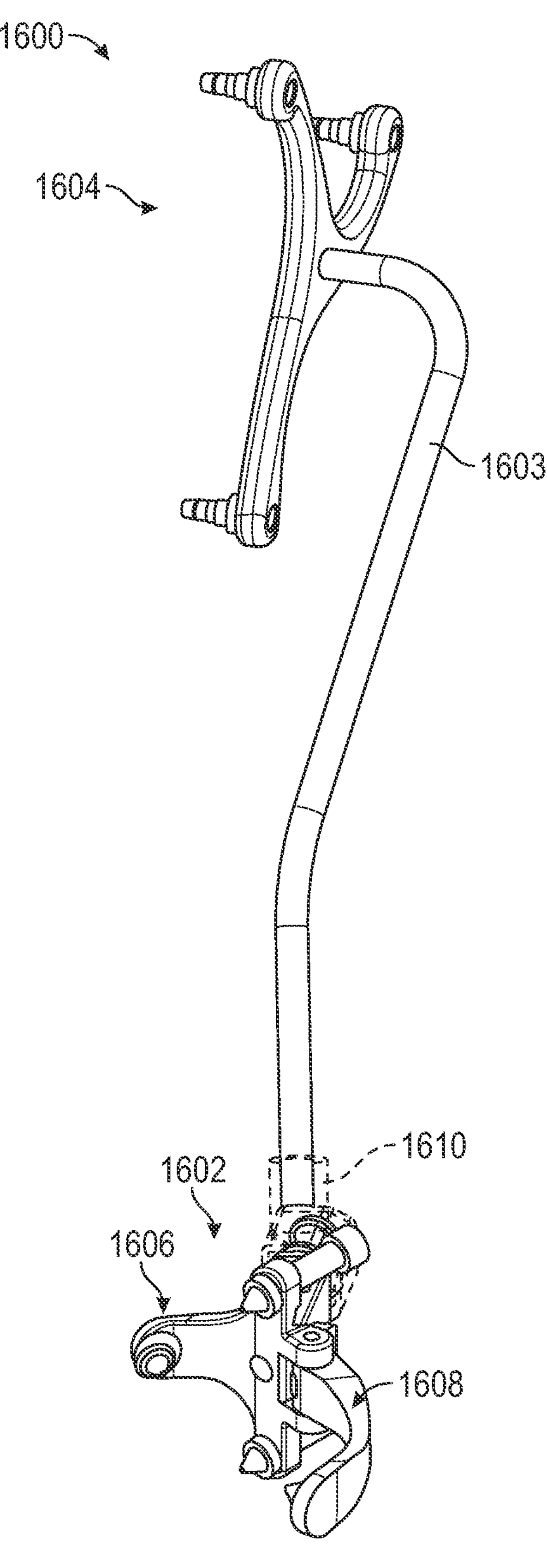
FIG. 16 illustrates an isometric view of a registration assembly a robotic surgical system.

FIG. 16 illustrates an isometric view of a registration assembly 1600 for a robotic surgical system, such as the robotic system 100. The registration assembly 1600 can be similar to the registration assemblies discussed above; the registration assembly 1600 can include first and second portions movable by an actuator. Any of the registration assemblies discussed above or below can be modified to include components of the registration assembly 1600.

More specifically, the registration assembly 1600 can include a plate assembly 1602 and a registration device 1604. The registration device 1604 can be similar to the registration devices discussed above. The plate assembly 1602 can include a first portion 1606 and a second portion 1608 that is movable with respect to the first portion 1606. The registration device 1604 can include a rod 1603, which can be an elongate member configured to connect the registration device 1604 to the plate assembly 1602 such as via a coupler 1610 of the plate assembly 1602. The rod 1603 can be shaped to orient a head of the registration device 1604 away from a surgical site.

In operation, the plate assembly 1602 can be secured to a bone, such as to a humerus. The registration device 1604 can then be secured to the plate assembly 1602, such as via the coupler 1610. The registration device 1604 can be oriented as desired with respect to the plate assembly 1602, such as to provide the robotic system 100 vision of the registration device 1604 when the registration assembly 1600 is secured to the bone. Further details of the registration assembly 1600 are discussed below.

Figure 17:
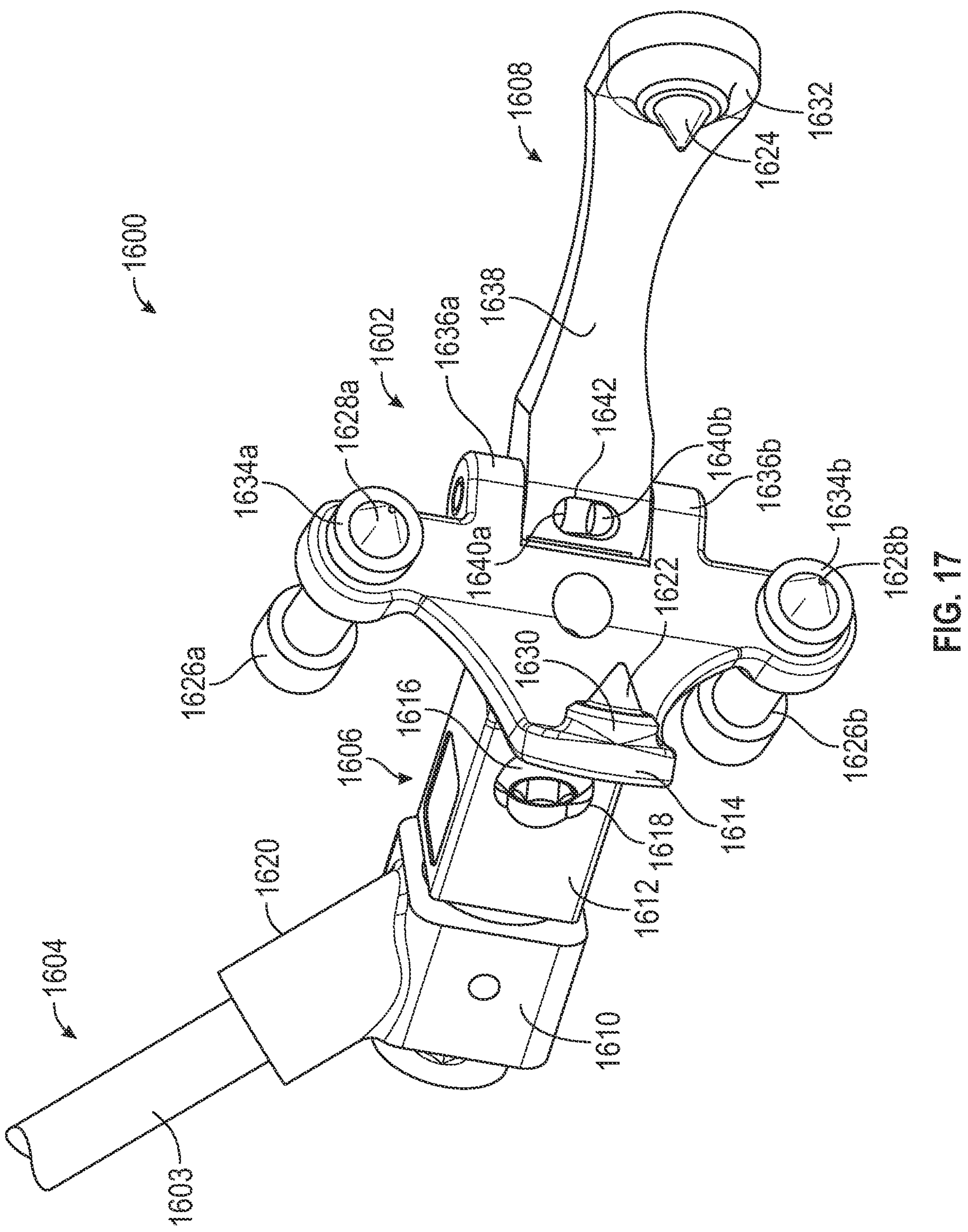
FIG. 17 illustrates an isometric view of a portion of a registration assembly for a robotic surgical system.

FIG. 17 illustrates an isometric view of a portion of the registration assembly 1600 for a robotic surgical system. The registration assembly 1600 can be consistent with the registration assembly 1600 of FIG. 16. FIG. 17 shows additional details of the registration assembly 1600. For example, FIG. 17 shows that the first portion 1606 can include a body 1612 and an arm 1614 extending away from the body 1612. The arm 1614 can be curved or angled such as to conform to a portion of a bone. The second portion 1608 can also be curved or angled such as to conform to a portion of the bone. The body 1612 and the registration device 1604 can be optionally integrally formed or made of, or from, a single piece. The first portion 1606, the second portion 1608, and the various components of the registration assembly 1600 can each be made of one or more of metals, polymers, or the like, and can be optionally made of bio-compatible materials (e.g., titanium or cobalt chromium).

FIG. 17 also shows that the registration assembly 1600 can include an actuator 1616 that can extend at least partially through a bore 1618 of the body 1612. As discussed in further detail below, the actuator 1616 can be engageable with the first portion 1606 (such as threadably engaged with the bore 1618) and the second portion 1608 to move the second portion 1608 toward a closed position, away from an open position.

FIG. 17 also shows that the coupler 1610 can be securable or secured to the body 1612 of the first portion 1606, such as to secure the registration device 1604 to the plate assembly 1602. The coupler 1610 can include a collar 1620 that can receive the rod 1603 therein.

FIG. 17 also shows that the first portion 1606 can include a bone spike 1622 and that the second portion 1608 can include a bone spike 1624. The bone spike 1622 and the bone spike 1624 can be configured to engage and at least partially penetrate bone to help secure the first portion 1606 and the second portion 1608 to the bone.

The registration assembly 1600 can also include inserts 1626*a* and 1626*b*. The inserts 1626*a* and 1626*b* can respectively include bone spikes 1628*a* and 1628*b* that can be configured to engage and at least partially penetrate bone to help secure the first portion 1606 to the bone. The inserts 1626*a* and 1626*b* can be configured to be inserted into (such as threadably engaged with) bores of the first portion 1606. The inserts 1626*a* and 1626*b* can extend through superior and inferior portions of the first portion 1606 and can be adjustable to apply a desired force to the bone via the spikes 1628*a* and 1628*b*.

Optionally, the first portion 1606 can include a stop 1630 for the bone spike 1622 and the second portion 1608 can include a stop 1632 for the bone spike 1624. The stops 1630 and 1632 can be connected to respective internal portions or surfaces of the first portion 1606 and the second portion 1608 and can extend therefrom. The inserts 1626*a* and 1626*b* can also include stops 1634*a* and 1634*b* that can be movable with the 1628*a* and 1628*b*. The stops 1630-1634 can each be engageable with a bone, such as the humerus 50, to help limit penetration of the bone spikes 1622, 1624, and 1628, respectively, into the bone. The use of four bone spikes can help the assembly 1600 to be stable and adaptive to a variety of bone morphologies. The use of four bone spikes can also provide four points of contact to help provide good control of all degrees of freedom.

FIG. 17 also shows how the second portion 1608 connects to the first portion 1606. The first portion 1606 can include knuckles 1636*a* and 16366 that can receive an end portion 1638 of the second portion 1608 therein. The knuckles 1636*a* and 16366 can also include bores configured to receive, respectively, pins 1640*a* and 1640*b* therein. The pins 1640 can be inserted into the end portion 1638 of the second portion 1608 to secure the second portion 1608 to the first portion 1606 and to form a hinge between the second portion 1608 and the first portion 1606 such that the second portion 1608 can rotate about the knuckles 1636. Optionally, the end portion 1638 can include a clean out bore 1642 for providing access for sterilization fluids for cleaning of the registration assembly 1600.

Figure 18:
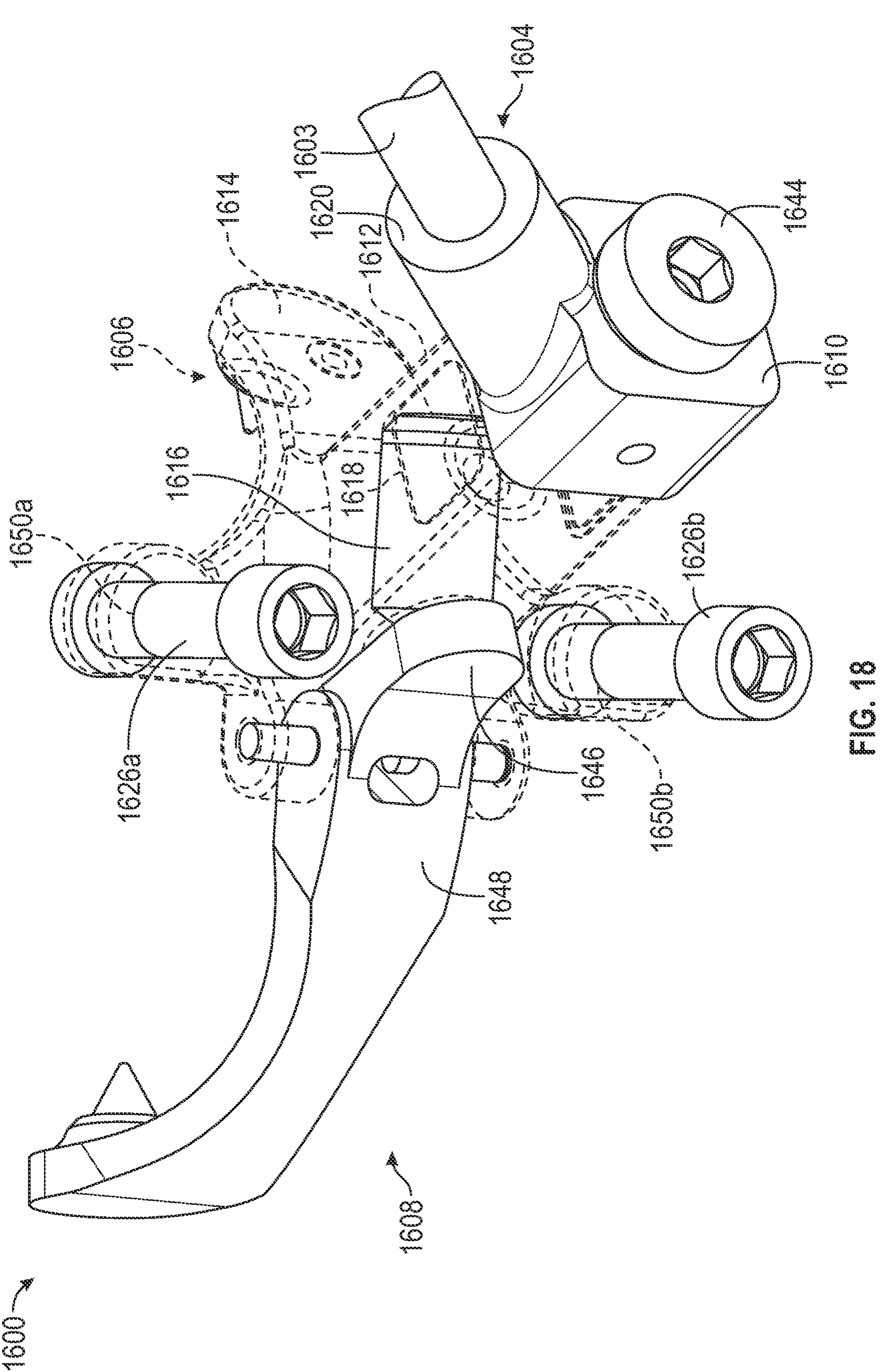
FIG. 18 illustrates an isometric view of a portion of a registration assembly for a robotic surgical system.

FIG. 18 illustrates an isometric view of a portion of the registration assembly 1600 for a robotic surgical system. The registration assembly 1600 can be consistent with the registration assembly 1600 of FIGS. 16-17. FIG. 18 shows additional details of the registration assembly 1600. For example, FIG. 18 shows that the registration device 1604 can include a fastener 1644 for securing the registration device 1604 to the body 1612, as discussed in further detail below.

FIG. 18 also shows how the actuator 1616 can extend through the bore 1618 of the body 1612 to engage the second portion 1608. This arrangement or connection can allow a user to drive the actuator 1616 to engage the second portion

1608 to move the second portion 1608 (about the hinge created by the knuckles 1636 and the end portion 1638) with respect to the first portion 1606 toward a closed position (and away from an open position).

FIG. 18 also shows that the second portion 1608 can include a tab 1646 that can extend from a body 1648 of the second portion 1608. When the actuator 1616 is moved to disengage the second portion 1608, the tab 1646 can be operated to move the second portion 1608 with respect to the first portion 1606 away from the closed position and toward the open position.

FIG. 18 also shows that the body 1612 of the first portion 1606 can include or define bores 1650*a* and 1650*b* extending through portions of the body 1612. The bores 1650*a* and 1650*b* can each be configured to receive the inserts 1626*a* and the 1626*b* therethrough. The bores 1650*a* and 1650*b* can optionally be threaded such as to allow the inserts 1626*a* and the 1626*b* to be threadably secured to the body 1612 and to allow the inserts 1626*a* and the 1626*b* to be loosened or tightened to applying a desired force with the bone spikes 1628*a* and 1628*b*.

Figure 19:
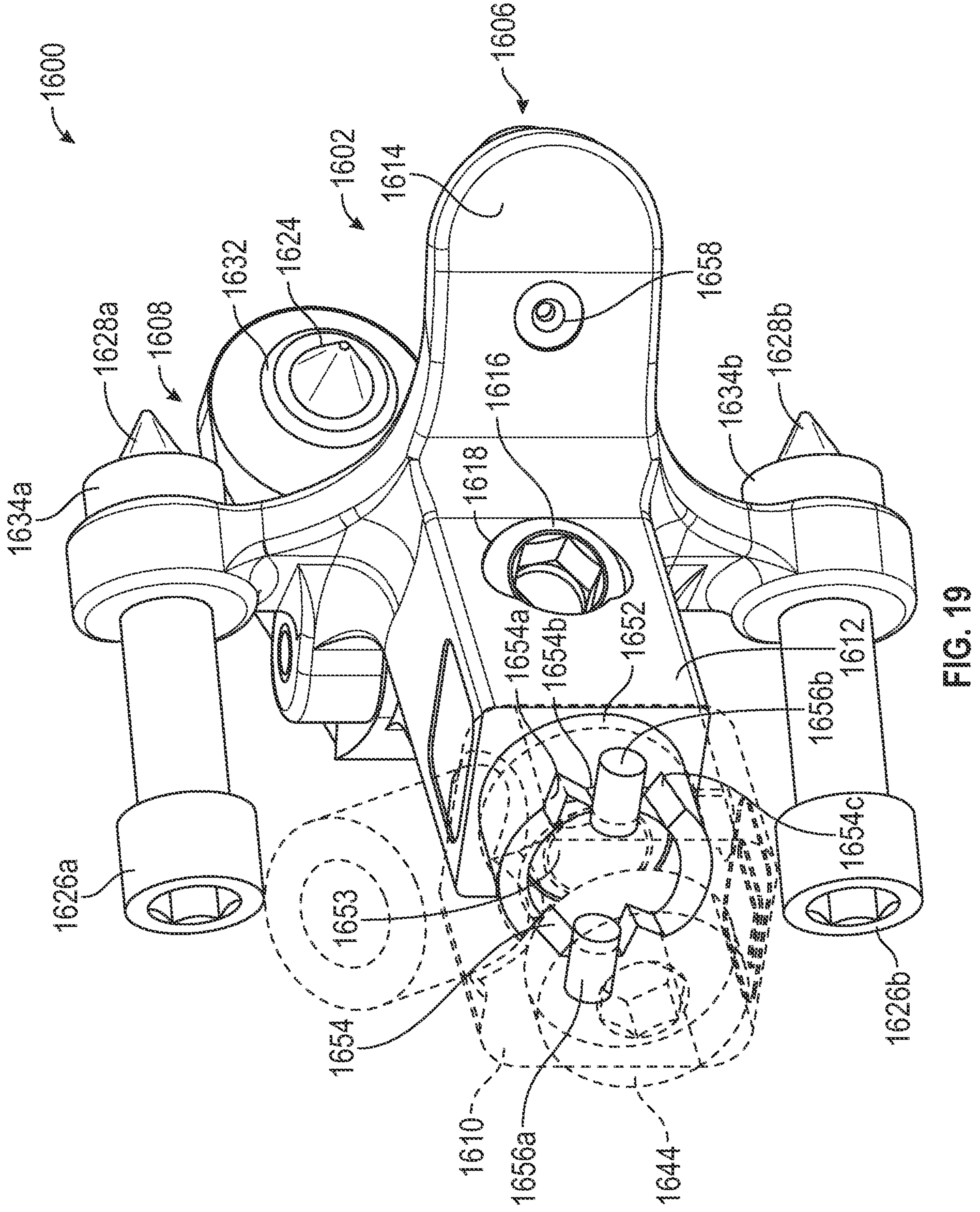
FIG. 19 illustrates an isometric view of a portion of a registration assembly for a robotic surgical system.

FIG. 19 illustrates an isometric view of a portion of a registration assembly for a robotic surgical system. The registration assembly 1600 can be consistent with the registration assembly 1600 of FIGS. 16-18. FIG. 19 shows additional details of the registration assembly 1600. For example, FIG. 19 shows that the registration device 1604 can include a crown 1652 for securing the coupler 1610 of the registration device 1604 to the body 1612.

The crown 1652 can include a threaded bore 1653 configured to receive the fastener 1644 therein to secure the coupler 1610 to the body 1612. The crown 1652 can also include notches 1654 (such as notches 1654*a*-1654*c*). Though six notches (two pairs of three notches) are shown, more or fewer notches can be used, such as 2, 4, 8, 10, 12, 14, 16, or the like. The notches 1654 can be configured to receive pins 1656*a* and 1656*b*, where the pins 1656 can be secured to the coupler 1610. The pins 1656 can be located on opposing sides of the coupler 1610 and can extend inward toward each other. The pins 1656 can be positionable in any of the notches 1654 to position the coupler 1610 (such as to position the registration device 1604) as desired with respect to the plate assembly 1602.

In operation of some examples, once the plate assembly 1602 is secured to the bone, the coupler 1610 can be placed over the crown 1652 and the pins 1656 can be oriented in the notches to orient the registration device 1604, as desired. For example, the pin 1656*b* can be position in the notch 1654*b* to orient the coupler 1610 and the registration device 1604 with respect to the body 1612 and therefore the plate assembly 1602. Once the registration device 1604 is oriented in a position that provides visibility of the registration device 1604 to the robotic system 100, the fastener 1644 can be tightened to secure the coupler 1610 in its oriented position.

FIG. 19 also shows that the arm 1614 of the first portion 1606 can include a reference bore 1658 configured to receive a reference device at least partially therein, as discussed in further detail below with reference to FIG. 20.

Figure 20:
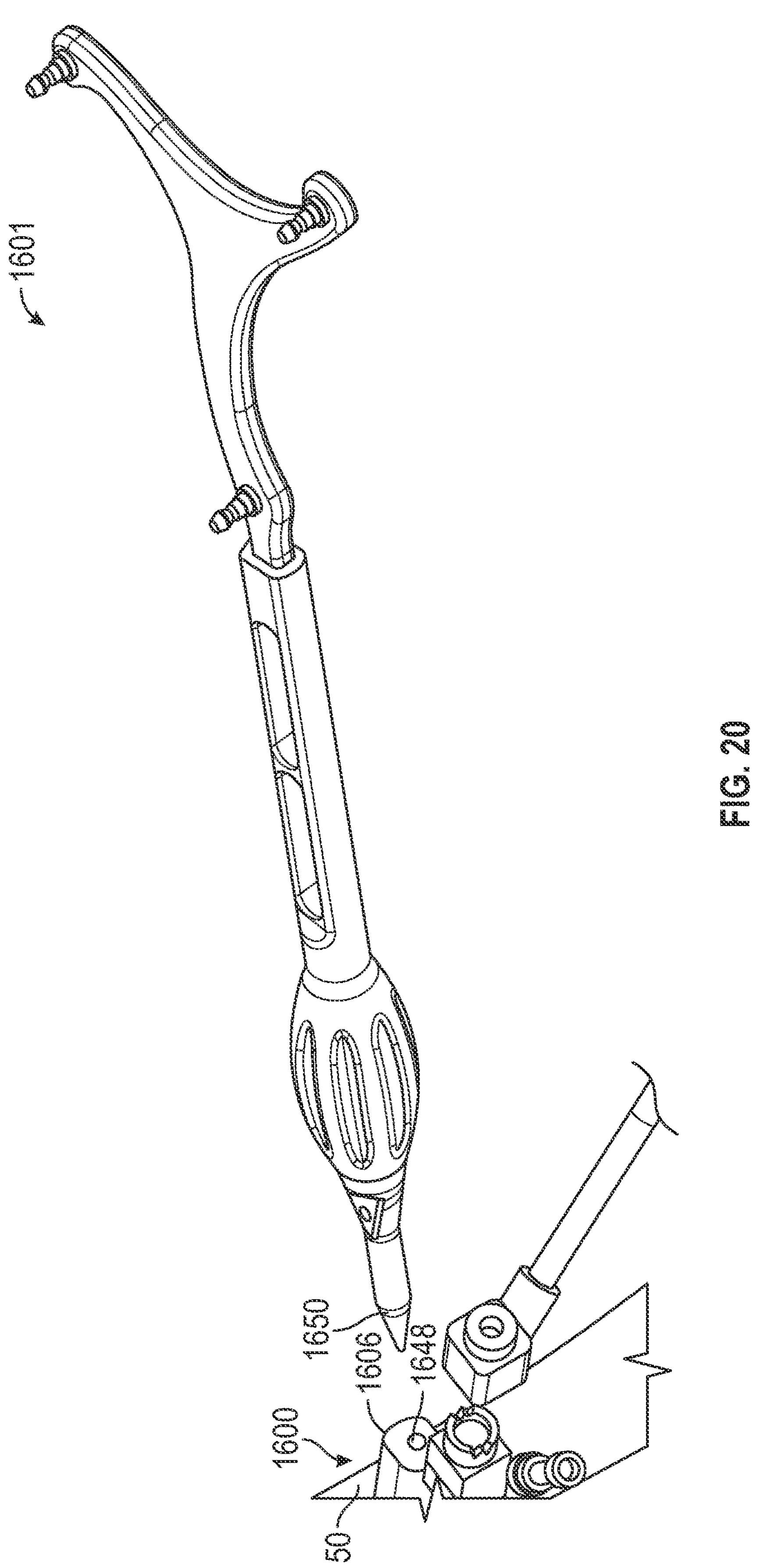
FIG. 20 illustrates an isometric view of a portion of a registration assembly for a robotic surgical system.

FIG. 20 illustrates an isometric view of a portion of a registration assembly for a robotic surgical system. The registration assembly 1600 can be consistent with the registration assembly 1600 of FIGS. 16-19. FIG. 20 shows additional details of the registration assembly 1600. For example, FIG. 20 shows that the registration assembly 1600 can be secured to a bone and shows how a reference registration device can be engaged with the registration assembly 1600.

As shown in FIG. 20, when the registration assembly 1600 is secured to the bone 50, a tip 1650 of a registration tool 1601 can be inserted into the body 1648 of the registration assembly 1600 such as to verify that a location of the registration assembly 1600 has not changed with respect to a bone, such as following a resection or other operational step performed on the bone. In this way, the location of the registration assembly 1600 can be quickly and easily confirmed following any step of an operation.

FIG. 2.1 illustrates an isometric view of a portion of a registration assembly 2100 for a robotic surgical system. The registration assembly 2100 can be similar to the registration assemblies discussed above; the registration assembly 2100 can include a locking device to move a wedge to clamp pins between the wedge and a plate to secure a registration device to the pins. Any of the registration assemblies discussed above or below can be modified to include components of the registration assembly 2100.

Figure 21:
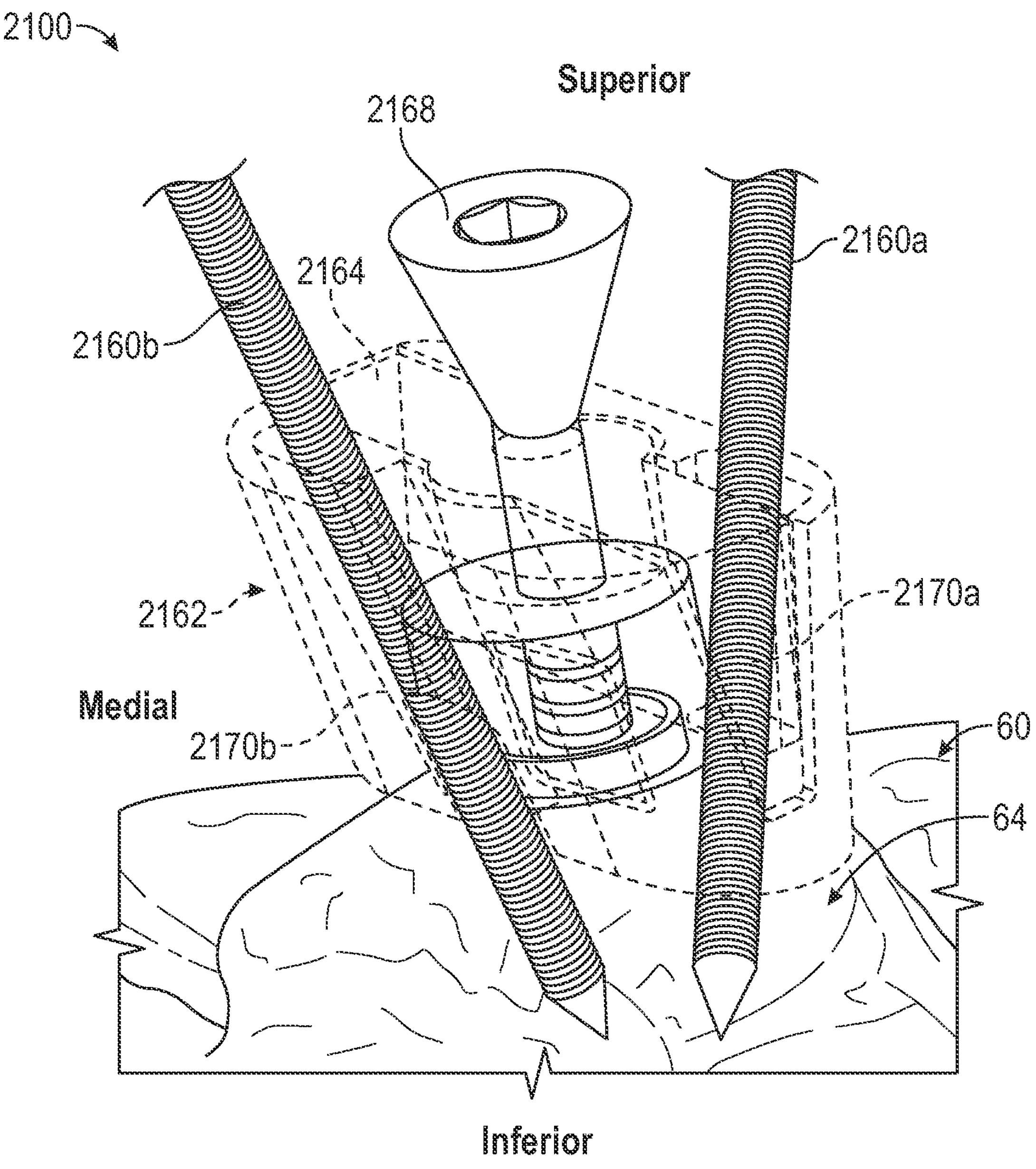
FIG. 21 illustrates an isometric view of a portion of a registration assembly for a robotic surgical system.

The registration assembly 2100 can include a pin 2160*a* and a pin 2160*b* (collectively referred to as pins 2160), a plate 2162, a registration device 2104 (shown in FIG. 22), a wedge 2164, a collar 2166 (shown in FIG. 22), and a locking device 2168. FIG. 21 also shows a scapula 60 and a coracoid 64. FIG. 21 further shows orientation indicators Superior, Interior, Medial, and Lateral.

The pins 2160, the plate 2162, the wedge 2164, the collar 2166, and the locking device 2168 can each be made of one or more of metals, polymers, or the like, and can be optionally made of biocompatible materials (e.g., titanium or cobalt chromium). The pins 2160 can each be elongate members including a sharp or pointed end that can be configured for insertion into bone, such as the coracoid 64 of the scapula 60. The plate 2162 can include a curved inferior surface that can be engageable with an outer surface of the coracoid 64. The plate 2162 can receive the pins 2160*a* and 2160*b* into bores 2170*a* and 2170*b*, which can extend at least partially through the plate 2162 and into the coracoid 64.

The pins 2160, the plate 2162, the wedge 2164, the collar 2166, and the locking device 2168 can together be configured to connect the registration device 2104 to the coracoid 64 for registration of the registration device 2104 and the scapula 60, such as with the robotic system 100. For example, the locking device 2168 can be operated to force the wedge 2164 to apply a force on the pins 2160 and the plate 2162, such as to clamp the pins 2160 between the wedge 2164 and the plate 2162, as discussed in further detail below.

Figure 22A:
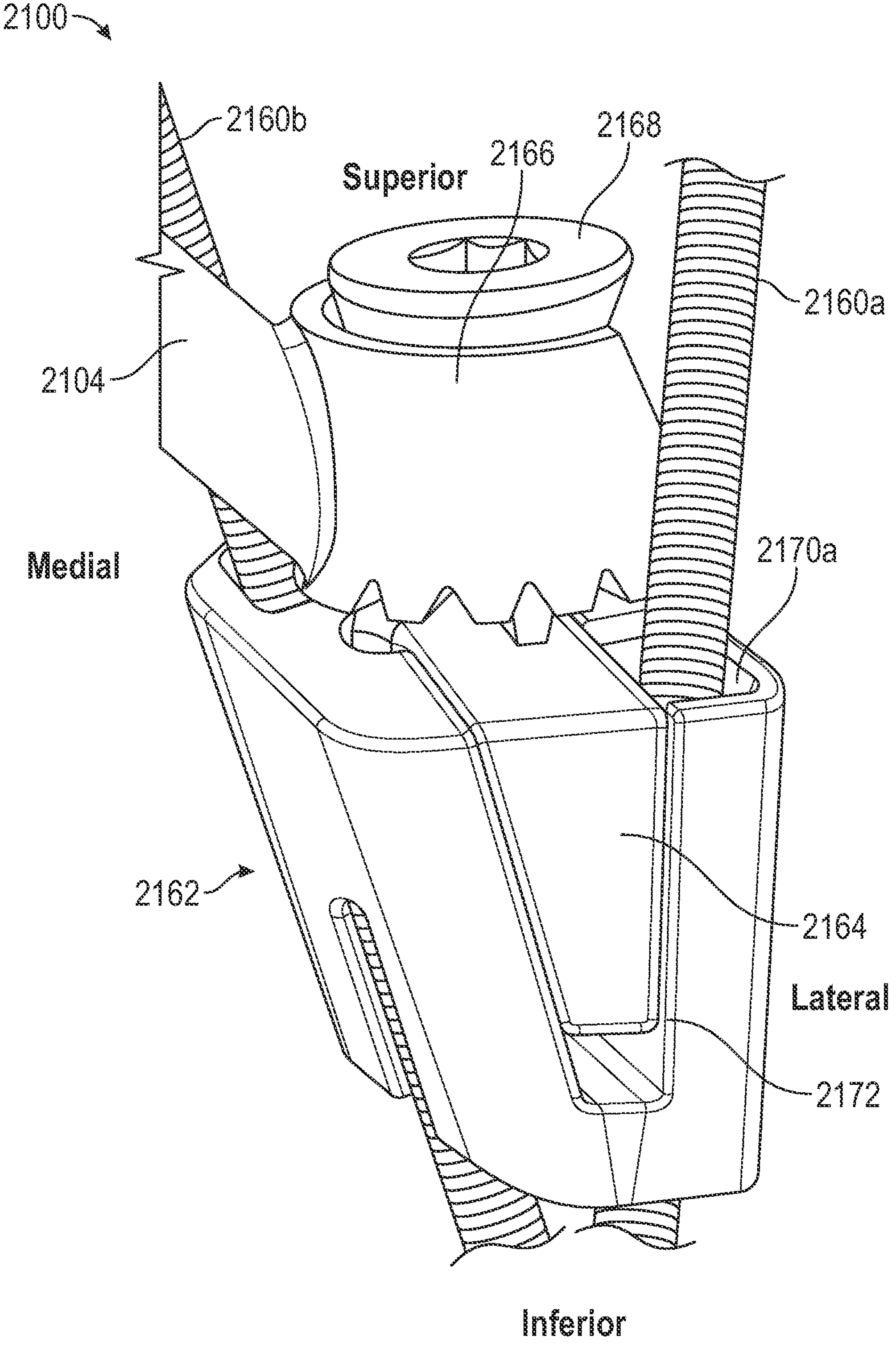
FIG. 22A illustrates an isometric view of a portion of a registration assembly for a robotic surgical system.
Figure 22B:
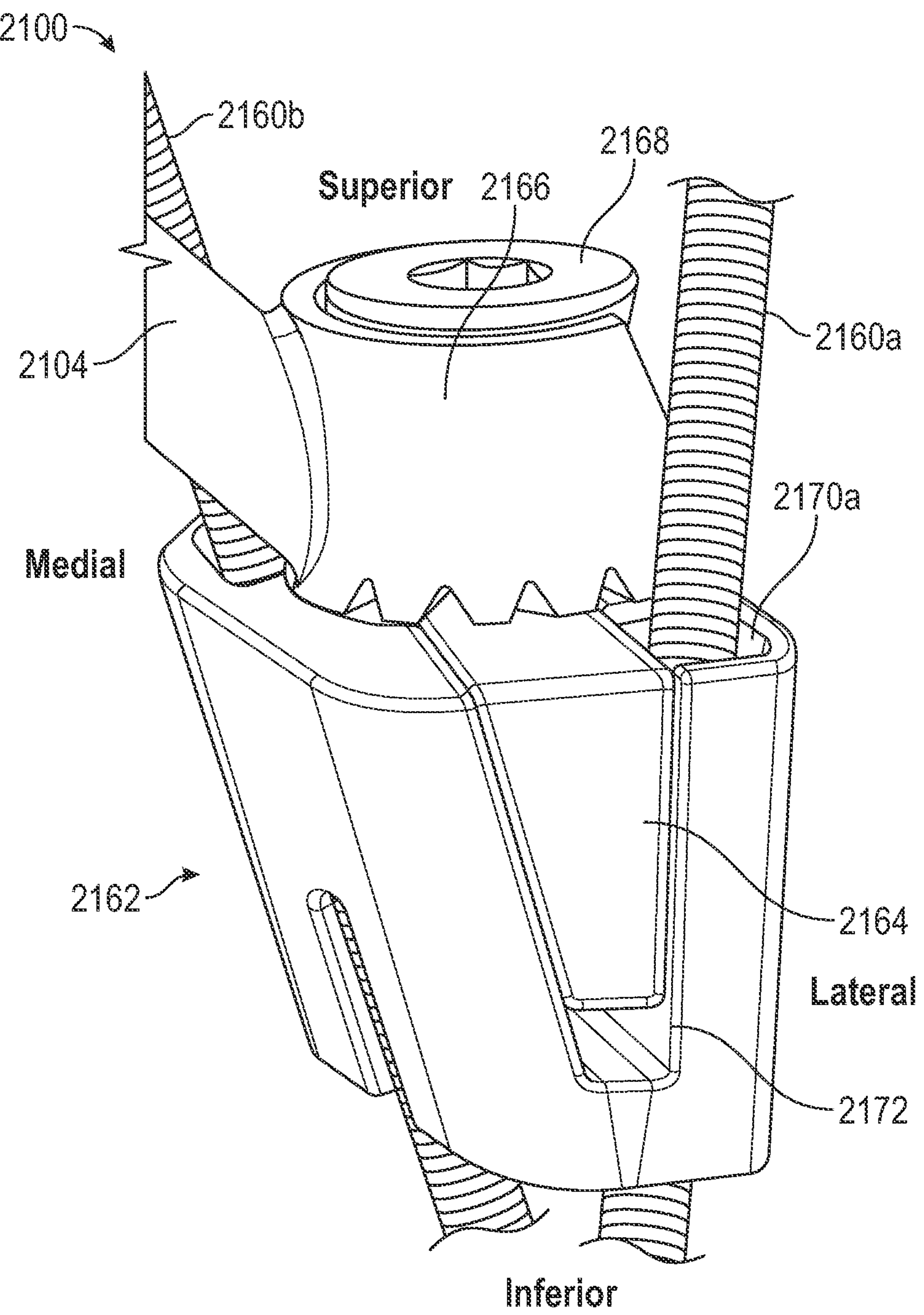
FIG. 22B illustrates an isometric view of a portion of a registration assembly for a robotic surgical system.

FIG. 22A illustrates an isometric view of a portion of the registration assembly 2100 for a robotic surgical system. FIG. 22B illustrates an isometric view of a portion of the registration assembly 2100 for a robotic surgical system. FIGS. 22A and 22B also shows orientation indicators Superior, Inferior, Medial, and Lateral. FIGS. 22A and 22B are discussed together below. The registration assembly 2100 can be consistent with the registration assembly 2100 of FIG. 21; FIGS. 22A and 22B show additional details of the registration assembly 2100, For example, FIGS. 22A and 22B show how the registration assembly 2100 can be operated to move from an unlocked position shown in FIG. 22A to a locked position shown in FIG. 22B.

More specifically, FIG. 22A shows that the wedge 2164 can be inserted into a slot 2172 of the plate 2162. FIG. 22A also shows that the pins 2160 can be inserted through the bores 2170 (as discussed with reference to FIG. 21). FIG. 22A also shows that the collar 2166 can be connected to the registration device 2104 (or can be a portion thereof). The collar 2166 can be positioned to at least partially surround the locking device 2168 to connect the registration device 2104 to the plate 2162 and the wedge 2164.

As shown in FIG. 22B, once the collar 2166 is positioned around the locking device 2168, the locking device 2168 can be secured or securable to the plate 2162. The locking device 2168 can be operated to move the locking device superiorly to inferiorly to engage the collar 2166, which can apply a force to the wedge 2164 to cause engagement between the wedge 2164, the pins 2160, and the plate 2162. Such action can cause the registration assembly 2100 to move from the unlocked shown in FIG. 22A to the locked position shown in FIG. 22B, where the collar 2166, the wedge 2164, and the plate 2162 can be secured to the pins 2160 to secure the registration assembly 2100 to the coracoid 64.

Figure 23:
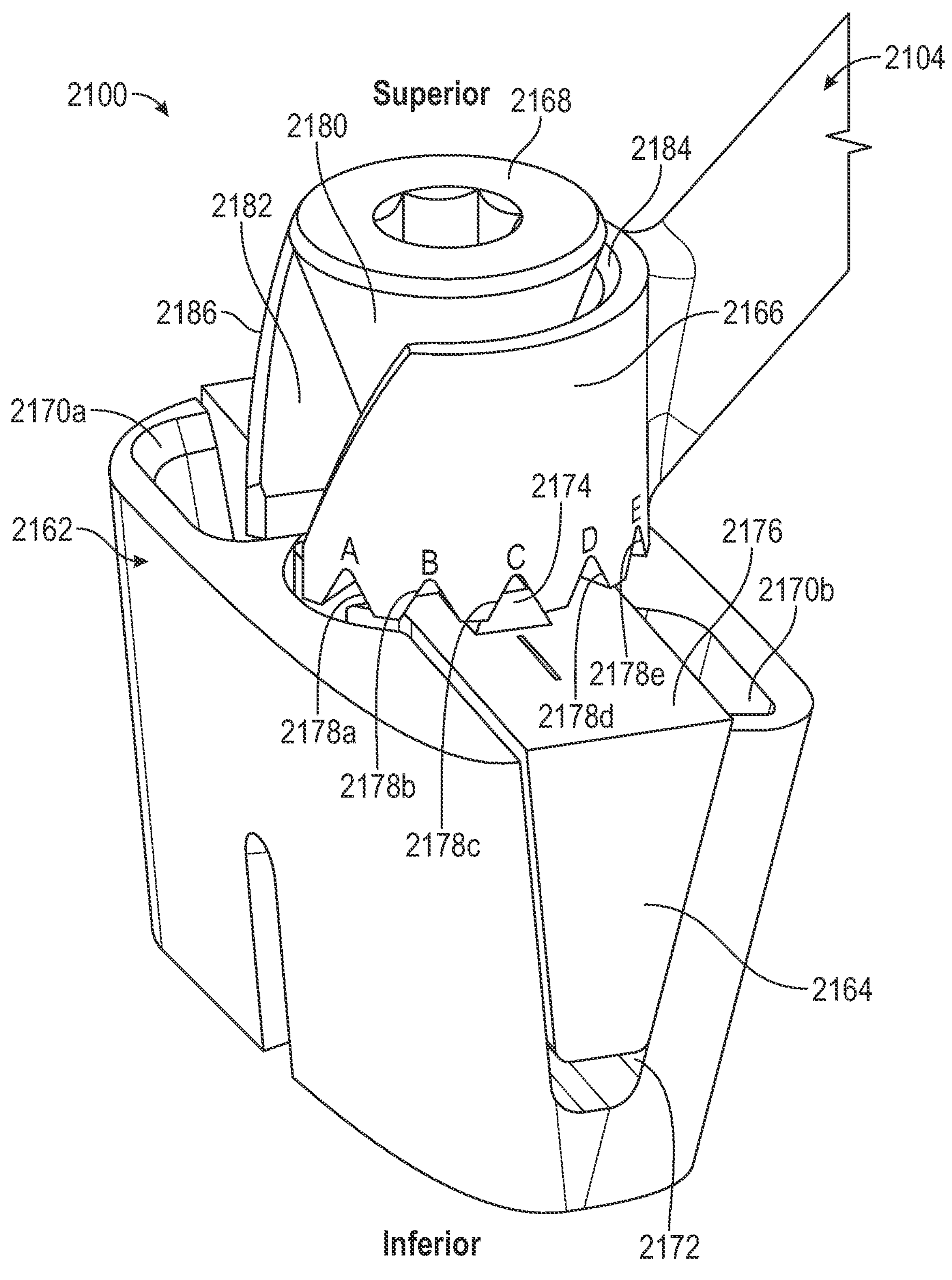
FIG. 23 illustrates an isometric view of a portion of a registration assembly for a robotic surgical system.

FIG. 23 illustrates an isometric view of a portion of the registration assembly 2100 for a robotic surgical system. The registration assembly 2100 can be consistent with the registration assembly 2100 of FIGS. 21-22B; FIG. 23 shows additional details of the registration assembly 2100. For example, FIG. 23 shows that the wedge 2164 can include a projection 2174 extending superiorly from a body 2176 of the wedge 2164. The projection 2174 can extend along at least a portion of a length of the body 2176 and can have a cross-sectional shape of a trapezoid. The projection 2174 can have other cross-sectional shapes.

FIG. 23 also shows that the collar can include a plurality of notches 2178*a*-2178*e*. The notches 2178 can each be shaped complimentary to the projection 2174 and the notches 2178 can optionally be shaped such that insertion of the projection 2174 into any of the notches 2178*a*-2178*e* causes the collar 2166 to be spaced away from the body 2176 and the plate 2162, which can help to ensure the force applied by the collar 2166 is transferred to the wedge 2164 and to the pins 2160 instead of from the collar 2166 to the plate 2162 (helping to avoid the force bypassing the wedge 2164).

Each of the notches 2178 can be selectably engageable with the projection 2174 to orient the collar 2166 and the registration device 2104 with respect to the plate 2162 and the pins (e.g., the pins 2160) and therefore the bone to which the pins are secured (e.g., the coracoid 64). That is, the collar 2166 can be rotated so that the projection 2174 extends into any of the notches 2178*a*-2178*e* to orient the collar 2166 and the registration device 2104 as desired before the locking device 2168 is moved to the locked position.

FIG. 23 also shows that the bores 2170 can have a square shape or a shape of a square with rounded edges or corners. Importantly, the bores can have a least one flat edge defined by the plate 2162. The wedge 2164 can define another flat edge of the bores such that the pins 2160, when inserted into the bores 2170 and when the wedge 2164 is moved to the locked position, can be compressed between flat edges of the wedge 2164 and flat edges the plate 2162 to help lock the wedge 2164 and the plate 2162 to the pins 2160.

FIG. 23 also shows that the wedge 2164 can have a shape that is complementary to the slot 2172. This can allow the wedge 2164 to increase engagement between the wedge 2164 and the pins 2160 as the wedge 2164 is translated into the slot 2172 as the locking device 2168 moves the wedge 2164 toward the locked position.

FIG. 23 also shows that the locking device 2168 can include a head having a tapered outer surface 2180 and shows that the locking device 2168 can include a tapered inner surface 2182 at least partially defining a bore 2184 extending at least partially through the collar 2166 (such as axially through the collar 2166). The tapered outer surface 2180 and the tapered inner surface 2182 can have complementary shapes such as to form a taper-to-taper engagement between the tapered outer surface 2180 and the tapered inner surface 2182. The taper-to-taper engagement can allow the locking device 2168 to effectively drive the collar 2166 toward the locked position while helping to reduce pressure on the surfaces of the locking device 2168 and the collar 2166.

FIG. 23 also shows that the collar 2166 can define an opening 2186 that can extend through at least a portion of the collar, circumferentially. That is, the collar 2166 can be circumferentially incomplete to define the opening 2186. The opening 2186 can thereby allow the collar 2166 to be inserted over the projection 2174 and at least partially around the locking device 2168 so that the registration device 2104 can be connected to the plate 2162 after the locking device 2168 is connected to the plate 2162, helping to reduce complexity or difficulty of assembly. The opening 2186 can be large enough to allow the locking device 2168 to pass through the collar 2166 without compromising the structural integrity of the collar 2166 during locking operations or while the collar 2166 is locked onto the wedge 2164.

In operation of some examples, the wedge 2164 can be inserted into the slot 2172 and the locking device 2168 can be secured to the plate 2162 (such as through the wedge 2164. Then, the registration device 2104 and the collar 2166 can be positioned such that the locking device 2168 passes through the opening 2186 and into the bore 2184. When in this (unlocked) position, the collar 2166 can be moved superiorly relative to the wedge 2164 (and to the projection 2174), allowing a user to position the projection 2174 in any of the notches 2178*a*-2178*e* to orient the registration device 2104 as desired (such as to ensure the robotic system 100 can detect the registration device 2104).

Once the projection 2174 is positioned in the desired notch (such as in the notch 2178*c*, as shown in FIG. 23), the locking device 2168 can be operated (e.g., driven to rotate) to translate inferiorly, causing engagement between the tapered outer surface 2180 and the tapered inner surface 2182 of the collar 2166. This engagement can cause the collar 2166 to apply a force to the projection 2174 causing the wedge 2164 to be driven inferiorly into the slot 2172 of the plate 2162 and causing the wedge 2164 to engage the pins 2160 to secure the wedge 2164 and the plate 2162 (and also the collar 2166 and the registration device 2104) to the pins 2160. Following a procedure or when an adjustment of the registration device 2104 is required, the locking device 2168 can be moved superiorly to allow the collar 2166 to be disengaged from the locking device 2168 and the projection 2174 and allowing the registration device 2104 to therefore be removed. Such a process can be repeated as desired or needed.

Figure 24:
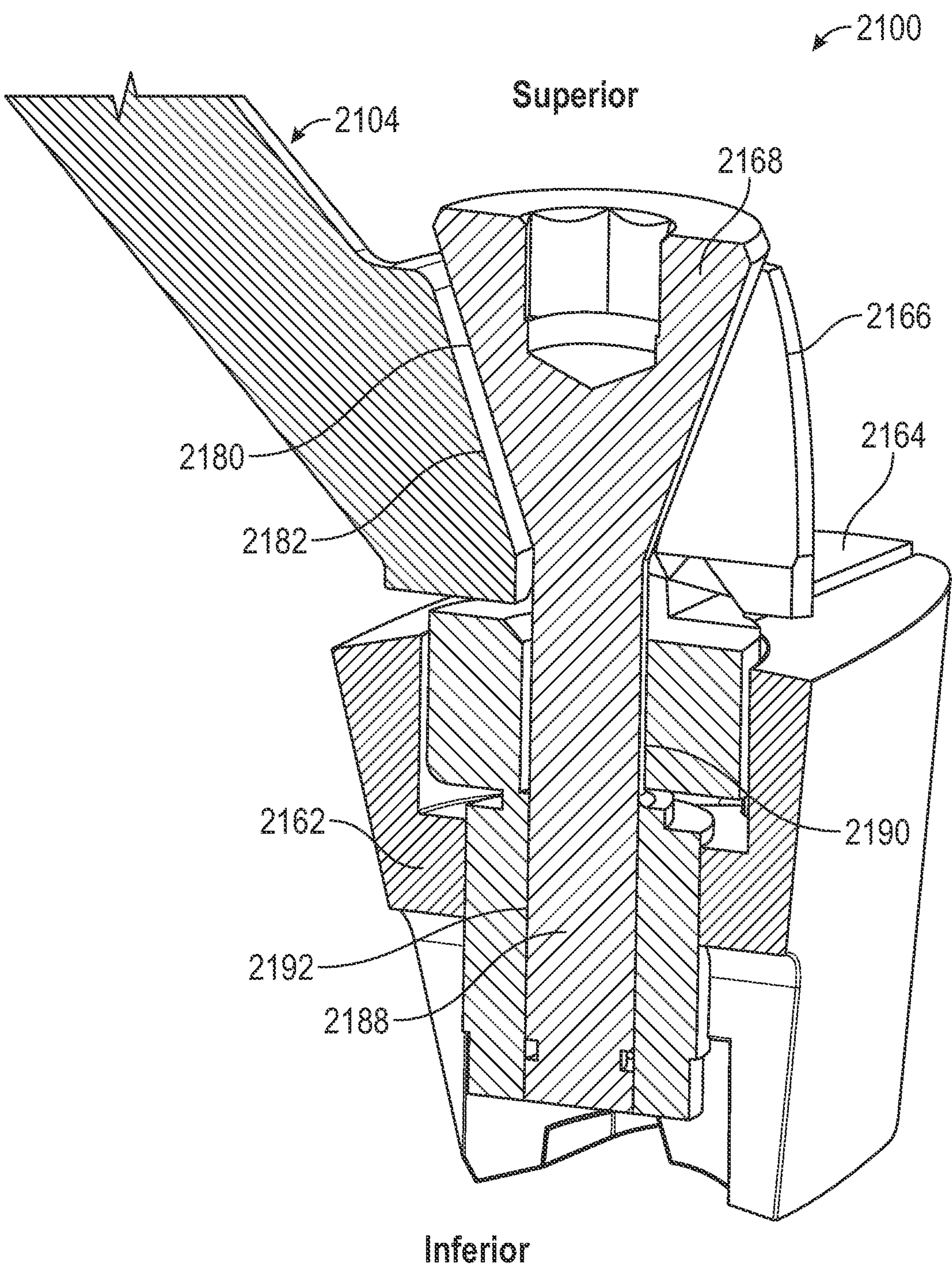
FIG. 24 illustrates an isometric cross-sectional view of a portion of a registration assembly for a robotic surgical system.

FIG. 24 illustrates an isometric cross-sectional view of a portion of the registration assembly 2100 for a robotic surgical system. The registration assembly 210) can be consistent with the registration assembly 2100 of FIGS. 21-3; FIG. 24 shows additional details of the registration assembly 2100. For example, FIG. 24 shows how the locking device 2168 can interact with the wedge 2164 and the plate 2162.

More specifically, the locking device 2168 can include a shank 2188 (or shaft) that can be optionally threaded. The shank 2188 can extend through a bore 2190 of the wedge 2164 and can extend into a threaded bore 2192 of the plate

2162, In operation, when the locking device 2168 is driven to rotate, the threaded engagement between the threaded bore 2192 and the shank 2188 can cause the locking device 2168 to move inferiorly relative to the plate 2162, which can cause the locking device locking device 2168 to engage the wedge 2164, causing the wedge 2164 to move inferiorly with the locking device 2168.

FIG. 24 also more clearly shows how the tapered outer surface 2180 of the locking device 2168 and the tapered inner surface 2182 of the collar 2166 can be shaped complementary to each other to form a taper-to-taper engagement when the locking device 2168 engages the collar 2166.

NOTES AND EXAMPLES

The following, non-limiting examples, detail certain aspects of the present subject matter to solve the challenges and provide the benefits discussed herein, among others.

Example 1 is a device for registering a bone for a robotic shoulder arthroplasty with a surgical robot, the device comprising: a plate engageable with an outer surface of a bone; a registration device connectable to the plate and configured to interface with the surgical robot for registration of the plate and the bone; a surgical cable configured to engage the bone; and a locking device connected to the plate and engageable with the surgical cable to secure at least a portion of the surgical cable to the plate.

In Example 2, the subject matter of Example 1 optionally includes wherein the locking device includes a cam movable to compress the surgical cable.

In Example 3, the subject matter of any one or more of Examples 1-2 optionally include wherein the locking device includes a clamp operable to compress the surgical cable.

In Example 4, the subject matter of any one or more of Examples 1-3 optionally include wherein the locking device includes an actuator rotatable to tighten the surgical cable to the plate.

Example 5, the subject matter of Example 4 optionally includes wherein the actuator includes a cleat engageable with the surgical cable to secure the surgical cable to the actuator.

In Example 6, the subject matter of any one or more of Examples 1-5 optionally include wherein the plate includes a bone spike extending from an internal portion of the plate, the bone spike engageable with the bone.

In Example 7, the subject matter of Example 6 optionally includes wherein the plate includes a stopper, the bone spike extending from the stopper away from the plate, the stopper engageable with the bone to limit penetration of the bone spike into the bone.

In Example 8, the subject matter of any one or more of Examples 1-7 optionally include wherein the plate is curved or angled.

In Example 9, the subject matter of any one or more of Examples 1-8 optionally include wherein the plate is includes: a hinge; a first portion connected to the hinge; and a second portion connected to the hinge and rotatable about the hinge with respect to the first portion.

In Example 10, the subject matter of any one or more of Examples 1-9 optionally include an arm connected to and extending from the plate, the arm engageable with a tuberosity of the bone to position the plate with respect to the bone.

In Example 11, the subject matter of any one or more of Examples 1-10 optionally include wherein the plate defines a drill bore extending therethrough.

In Example 12, the subject matter of Example 11 optionally includes wherein the plate includes a bone spike extending from an internal portion of the plate, the bone spike adjacent to the drill bore, and the bone spike insertable into a bore of the bone created using the drill bore.

In Example 13, the subject matter of Example 12 optionally includes wherein the plate includes a spike stopper, the bone spike extending from the spike stopper away from the plate, the stopper engageable with the bone to limit penetration of the bone spike into the bone.

In Example 14, the subject matter of any one or more of Examples 12-13 optionally include wherein the plate includes a drill stopper, the drill bore extending through the drill stopper, the drill stopper engageable with a drill to limit a depth of drilling into the bone.

Example 15 is a device for registering a bone for a robotic shoulder arthroplasty with a surgical robot, the device comprising: a plate engageable with an outer surface of a bone; a pair of collars connected to and extending from the plate, the collars each defining a bore extending therethrough; a pair of pins insertable into the bone through the bores of the collars, respectively; a first housing member engageable with the plate; a second housing member engageable with the plate and the first housing member; a locking device connectable to the second housing member and engageable with the first housing member to cause the first housing member and the second housing member to engage the pair of pins to secure the first housing member, the second housing member, and the plate to the pins; and a registration device connectable to the first housing member and configured to interface with the surgical robot for registration of the plate and the bone.

In Example 16, the subject matter of Example 15 optionally includes wherein the locking device is a screw threadably engageable with the first housing member and the second housing member.

In Example 17, the subject matter of any one or more of Examples 15-16 optionally include wherein the first housing member and the second housing member together define a first housing bore and a second housing bore to receive the pair of pins therethrough, respectively, when the pins are located in the collars.

In Example 18, the subject matter of Example 17 optionally includes wherein operation of the locking device reduces a size of the first housing bore and the second housing bore.

In Example 19, the subject matter of any one or more of Examples 17-18 optionally include wherein the first housing bore and the second housing bore have a square shape.

In Example 20, the subject matter of any one or more of Examples 17-19 optionally include a pair of wings connected to opposing sides of the plate and extending inferiorly therefrom.

In Example 21, the subject matter of Example 20 optionally includes wherein the plate includes first and second notches together configured to locate the plate on the bone.

Example 22 is a device for registering a bone for a robotic shoulder arthroplasty with a surgical robot, the device comprising: a plate engageable with an outer surface of a bone; a registration device connectable to the plate and configured to interface with the surgical robot for registration of the plate and the bone; a surgical cable configured to engage the bone and including a distal end portion; a locking device connected to the plate and engageable with the surgical cable to secure at least a portion of the surgical cable to the plate; and a spreader engageable with the locking device and the distal portion to tension the surgical cable on the bone.

In Example 23, the subject matter of Example 22 optionally includes wherein the locking device is a uni-directional locking mechanism.

In Example 24, the subject matter of any one or more of Examples 22-23 optionally include wherein the spreader is a surgical spreader.

In Example 25, the subject matter of any one or more of Examples 22-24 optionally include wherein the plate includes a bone spike extending from an internal portion of the plate, the bone spike engageable with the bone.

In Example 26, the subject matter of Example 22 optionally includes wherein the plate includes a stopper, the bone spike extending from the stopper away from the plate, the stopper engageable with the bone to limit penetration of the bone spike into the bone.

Example 27 is a device for registering a bone for a robotic shoulder arthroplasty with a surgical robot, the device comprising: a plate engageable with an outer surface of a bone, the plate comprising: a hinge; a first portion connected to the hinge and engageable with a first portion of the bone; and a second portion engageable with a second portion of the bone, connected to the hinge, and rotatable about the hinge with respect to the first portion; a registration device connectable to the plate and configured to interface with the surgical robot for registration of the plate and the bone; and a locking device connected to the plate and engageable with the first portion and the second portion to limit movement of the first portion with respect to the second portion.

In Example 28, the subject matter of Example 27 optionally includes wherein the first portion and the second portion are rotatable about the hinge between an open position and a closed position.

In Example 29, the subject matter of Example 28 optionally includes a biasing element connected to the first portion and the second portion to bias the first portion and the second portion toward the closed position.

In Example 30, the subject matter of Example 29 optionally includes wherein the biasing element is a coil compression spring and the locking device is a screw extending at least partially through the coil compression spring.

In Example 31, the subject matter of any one or more of Examples 28-30 optionally include a coupler releasably securable to the plate, the coupler configured to releasably secure the registration device to the plate.

In Example 32, the subject matter of any one or more of Examples 27-31 optionally include wherein the plate includes a bone spike extending from an internal portion of the plate, the bone spike engageable with the bone.

In Example 33, the subject matter of Example 32 optionally includes wherein the plate includes a stopper, the bone spike extending from the stopper away from the plate, the stopper engageable with the bone to limit penetration of the bone spike into the bone.

In Example 34, the subject matter of any one or more of Examples 27-33 optionally include wherein one or more of the first portion or the second portion of the plate is curved or angled.

In Example 35, the subject matter of any one or more of Examples 27-34 optionally include wherein the plate defines a drill bore extending therethrough.

In Example 36, the subject matter of Example 35 optionally includes wherein the plate includes a bone spike extending from an internal portion of the plate, the bone spike adjacent to the drill bore, and the bone spike insertable into a bore of the bone created using the drill bore.

Example 37 is a device for registering a bone for a robotic shoulder arthroplasty with a surgical robot, the device comprising: a first portion engageable with a first portion of a bone; and a second portion engageable with a second portion of the bone, the second portion connected to the first portion and rotatable with respect to the first portion; a registration device connectable to the first portion and configured to interface with the surgical robot for registration of the device and the bone; and an actuator engageable with the first portion and the second portion to move the second portion toward a closed position away from an open position.

In Example 38, the subject matter of Example 37 optionally includes wherein the first portion includes a bone spike extending from an internal portion of the first portion, the bone spike engageable with the bone.

In Example 39, the subject matter of Example 38 optionally includes wherein the first portion includes a stopper connected to the internal portion, the bone spike extending away from the stopper, the stopper engageable with the bone to limit penetration of the bone spike into the bone.

In Example 40, the subject matter of any one or more of Examples 3839 optionally include a second bone spike threadably securable to the first portion and engageable with the bone.

In Example 41, the subject matter of any one or more of Examples 37-40 optionally include wherein the second portion includes a third bone spike engageable with the bone.

In Example 42, the subject matter of any one or more of Examples 37-41 optionally include wherein the first portion is curved.

In Example 43, the subject matter of any one or more of Examples 37-42 optionally include a tab operable to move the second portion toward the open position.

In Example 44, the subject matter of any one or more of Examples 37-43 optionally include a coupler releasably securable to the first portion, the coupler configured to releasably secure the registration device to the first portion.

In Example 45, the subject matter of any one or more of Examples 37-44 optionally include wherein the first portion includes a reference bore configured to receive a reference device at least partially therein.

In Example 46, the subject matter of any one or more of Examples 37-45 optionally include wherein the actuator is threadably engageable with the first portion to engage the second portion.

Example 47 is an assembly for registering a bone for a robotic shoulder arthroplasty with a surgical robot, the assembly comprising: a plate engageable with an outer surface of a bone; a pair of bores extending through the plate; a pair of pins insertable into the bone through the pair of bores; a wedge at least partially insertable into the plate and engageable with the pins; a collar engageable with the wedge; a locking device securable to the plate to engage the collar to secure the collar, the wedge, and the plate to the pins; and a registration device connectable to the collar and configured to interface with the surgical robot for registration of the plate and the bone.

In Example 48, the subject matter of Example 47 optionally includes wherein the locking device is a screw threadably engageable with the plate.

In Example 49, the subject matter of any one or more of Examples 47-48 optionally include wherein operation of the locking device causes engagement between the wedge and the plate with the pins.

In Example 50, the subject matter of any one or more of Examples 47-49 optionally include wherein the pair of bores each have a square shape.

In Example 51, the subject matter of any one or more of Examples 47-50 optionally include wherein an inferior portion of the plate is curved.

In Example 52, the subject matter of any one or more of Examples 47-51 optionally include wherein the wedge includes a projection extending superiorly from a body of the wedge, and wherein the collar includes a plurality of notches selectably engageable with the projection of the wedge to orient the registration device with respect to the plate.

In Example 53, the subject matter of any one or more of Examples 47-52 optionally include wherein the collar includes a bore extending axially therethrough and configured to receive the locking device at least partially therethrough.

In Example 54, the subject matter of Example 53 optionally includes wherein the bore includes a circumferential opening to receive the locking device into the bore.

In Example 55, the subject matter of any one or more of Examples 53-54 optionally include wherein the bore is tapered complementary to a head of the locking device.

In Example 56, the apparatuses or method of any one or any combination of Examples 1-55 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A device for registering a bone for a robotic shoulder arthroplasty with a surgical robot, the device comprising:

a first portion engageable with a first portion of a bone, the first portion including:

a stopper connected to an internal portion of the first portion and extending therefrom; and a bone spike extending from the stopper, the bone spike engageable with the bone, the stopper engageable with the bone to limit penetration of the bone spike into the bone;

a second portion engageable with a second portion of the bone, the second portion connected to the first portion and rotatable with respect to the first portion;

a registration device connectable to the first portion and configured to interface with the surgical robot for registration of the device and the bone;

an actuator engageable with the first portion and the second portion to move the second portion toward a closed position away from an open position;

an insert connected to one or more of the first portion and the second portion; and a second bone spike connected to the insert and engageable with the bone, the insert operable to move the bone spike with respect to the first portion and the second portion when the bone spike is engaged with the bone to adjust a force applied to the bone by the bone spike.

2. The device of claim 1, wherein the second portion includes a third bone spike engageable with the bone.

3. The device of claim 1, wherein the first portion is curved.

4. The device of claim 1, further comprising:

a tab operable to move the second portion toward the open position.

5. The device of claim 1, further comprising:

a coupler releasably securable to the first portion, the coupler configured to releasably secure the registration device to the first portion.

6. The device of claim 1, wherein the first portion includes a reference bore configured to receive a reference device at least partially therein.

7. The device of claim 1, wherein the actuator is threadably engageable with the first portion to engage the second portion.

8. A device for registering a bone for a robotic shoulder arthroplasty with a surgical robot, the device comprising:

a first portion engageable with a first portion of a bone;

a second portion engageable with a second portion of the bone, the second portion connected to the first portion and rotatable with respect to the first portion;

a registration device connectable to the first portion and configured to interface with the surgical robot for registration of the device and the bone;

an actuator engageable with the first portion and the second portion to move the second portion toward a closed position away from an open position;

an insert connected to one or more of the first portion and the second portion; and a bone spike connected to the insert and engageable with the bone, the insert operable to move the bone spike with respect to the first portion and the second portion when the bone spike is engaged with the bone to adjust a force applied to the bone by the bone spike.

9. The device of claim 8, wherein the first portion includes a second bone spike extending from an internal portion of the first portion, the second bone spike engageable with the bone, and wherein the first portion includes a stopper connected to the internal portion, the second bone spike extending away from the stopper, the stopper engageable with the bone to limit penetration of the second bone spike into the bone.

10. The device of claim 8, further comprising:

a tab operable to move the second portion toward the open position.

11. The device of claim 8, further comprising:

a second bone spike threadably securable to the first portion and engageable with the bone.

12. The device of claim 11, wherein the second portion includes a third bone spike engageable with the bone.

13. The device of claim 8, wherein the first portion is curved.

14. The device of claim 8, further comprising:

a tab operable to move the second portion toward the open position.

15. The device of claim 8, further comprising:

a coupler releasably securable to the first portion, the coupler configured to releasably secure the registration device to the first portion.

16. The device of claim 8, wherein the first portion includes a reference bore configured to receive a reference device at least partially therein.

17. The device of claim 8, wherein the actuator is threadably engageable with the first portion to engage the second portion.

* * * * *